(12) United States Patent
Van Dam et al.

(10) Patent No.: US 9,193,640 B2
(45) Date of Patent: Nov. 24, 2015

(54) DIGITAL MICROFLUIDIC PLATFORM FOR RADIOCHEMISTRY

(71) Applicant: THE REGENTS OF THE UNIVERSITY OF CALIFORNIA, Oakland, CA (US)

(72) Inventors: R. Michael Van Dam, Los Angeles, CA (US); Chang-Jin Kim, Beverly Hills, CA (US); Supin Chen, Los Angeles, CA (US); Huijiang Ding, Arcadia, CA (US); Gaurav Jitendra Shah, Los Angeles, CA (US); Pei Yuin Keng, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/643,151

(22) Filed: Mar. 10, 2015

(65) Prior Publication Data

US 2015/0203416 A1 Jul. 23, 2015

Related U.S. Application Data

(63) Continuation of application No. 13/500,785, filed as application No. PCT/US2010/002756 on Oct. 15, 2010, now Pat. No. 9,005,544.

(60) Provisional application No. 61/252,095, filed on Oct. 15, 2009.

(51) Int. Cl.
*G01N 1/10* (2006.01)
*C07B 59/00* (2006.01)

(52) U.S. Cl.
CPC ............. *C07B 59/001* (2013.01); *C07B 59/005* (2013.01); *C07B 2200/05* (2013.01)

(58) Field of Classification Search
CPC .................. B01L 3/502792; B01L 2400/0415; B01L 2400/0417; B01J 19/0093; B01J 2219/00783; B01J 2219/00853; B01J 2219/00873
USPC ............. 422/501, 502, 503, 504; 436/53, 180
See application file for complete search history.

(56) References Cited

U.S. PATENT DOCUMENTS

| | | | |
|---|---|---|---|
| 6,565,727 | B1 | 5/2003 | Shenderov |
| 2003/0211009 | A1 | 11/2003 | Buchanan |
| 2004/0022696 | A1 | 2/2004 | Zigler et al. |
| 2007/0241068 | A1 | 10/2007 | Pamula et al. |
| 2008/0233018 | A1* | 9/2008 | van Dam et al. ............... 422/159 |

FOREIGN PATENT DOCUMENTS

| | | |
|---|---|---|
| JP | 03-11617 | 1/1991 |
| WO | WO 2004/030820 | 4/2004 |

(Continued)

OTHER PUBLICATIONS

Office Action dated Jul. 1, 2014 in Japanese Patent Application No. 2012-534166, in the name of The Regents of the University of California, including an English translation of the office action provided by Kita-Aoyama International Patent Bureau (14pages).

(Continued)

*Primary Examiner* — Jill Warden
*Assistant Examiner* — Dwayne K Handy
(74) *Attorney, Agent, or Firm* — Vista IP Law Group LLP

(57) ABSTRACT

Disclosed herein are methods of performing microchemical reactions and electro-wetting-on-dielectric devices (EWOD devices) for use in performing those reactions. These devices and method are particularly suited for preparing radiochemical compounds, particularly compounds containing $^{18}F$.

13 Claims, 15 Drawing Sheets

(56) References Cited

FOREIGN PATENT DOCUMENTS

| WO | WO 2006/018088 | 2/2006 |
|----|----------------|--------|
| WO | WO 2006/071470 | 7/2006 |
| WO | WO 2006/124458 | 11/2006 |
| WO | WO 2007/120241 | 10/2007 |

OTHER PUBLICATIONS

Elizarov, Arkadij, Microreactors for Radiopharmaceutical Synthesis, Lab Chip, 2009, 9, 1326-1333.

Fan, Shih-Kang et al., EWOD Driving of Droplet on NxM Grid Using Single-Layer Electrode Patterns, Solid-State Sensor, Actuator and Microsystems Workshop, Hilton Head Island, South Carolina, Jun. 2-6, 2002.

Audrain, Helene, Positron Emission Tomography (PET) and Microfluidic Devices: A Breakthrough on the Microscale?, Angew. Chem. Int. Ed. 2007, 46, 1772-1775.

Lee, Chung-Chen et al., Multistep Synthesis of a Radiolabeled Imaging Probe Using Integrated Microfluidics, Science, vol. 310, Dec. 16, 2005, 1793-1796.

\* cited by examiner

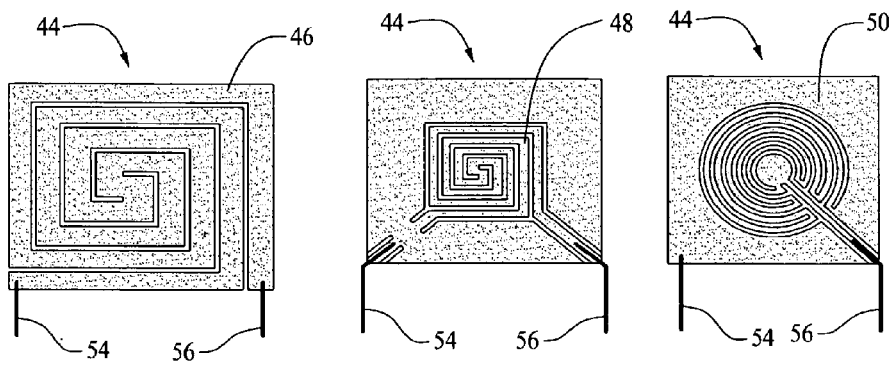
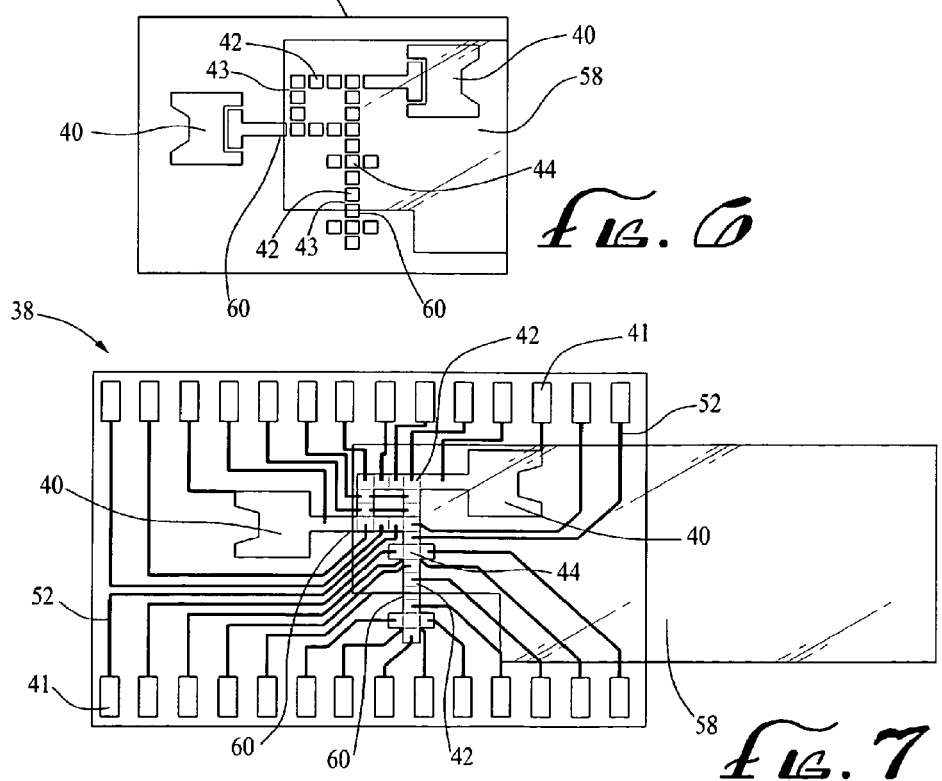

DIGITAL MICROFLUIDIC PLATFORM FOR RADIOCHEMISTRY

RELATED APPLICATIONS

This application is a continuation of U.S. patent application Ser. No. 13/500,785, filed Apr. 6, 2012, now U.S. Pat. No. 9,005,544, which claims priority to U.S. National Stage filing under 35 U.S.C. §371 of International Application No. PCT/US2010/002756, filed Oct. 15, 2010, which claims priority to U.S. Provisional Patent Application No. 61/252,095 filed on Oct. 15, 2009. The contents of the aforementioned applications are hereby incorporated herein by reference in their entirety. Priority to the aforementioned applications are hereby expressly claimed in accordance with 35 U.S.C. §§119, 120, 365 and 371 and any other applicable statutes.

STATEMENT REGARDING FEDERALLY SPONSORED RESEARCH AND DEVELOPMENT

This invention was made with Government support under CA119347 and RR020070, awarded by the National Institutes of Health and DE-SC0005056, awarded by the United States Department of Energy. The Government has certain rights in the invention.

Benefit of U.S. Provisional Application 61/252,095 filed Oct. 15, 2009 is claimed. This invention was made with Government support under Grant No. CA119347 and Grant No. RR020070 awarded by the National Institute of Health (NIH). The federal government may have certain rights in the invention.

The use of microfluidic devices for performing chemical reactions, particularly radiochemical reactions and more particularly the production of tracers for positron emission tomography (PET) is described in A. M. Elizarov, "Microreactors for Radiopharmaceutical Synthesis," *Lab on a Chip*. vol. 9, no. 10, pp. 1326-1333, May, 2009; C.-C. Lee, G. Sui, A. Elizarov et al., "Multistep Synthesis of a Radiolabeled Imaging Probe Using Integrated Microfluidics," *Science*, vol. 310, no. 5755, pp. 1793-1796, Dec. 16, 2005, 2005 and A. Helene, "Positron Emission Tomography (PET) and Microfluidic Devices: A Breakthrough on the Microscale?," *Angewandte Chemie International Edition*. vol. 46, no. 11, pp. 1772-1775 (2007), all of which are incorporated in their entirety by reference herein. Microfluidic devices provide the option of reducing reagent usage, increasing control over reactions (e.g. heating and mixing), reducing overall system size, when used in radiochemical synthesis, reducing radiation shielding needs, and they provide practical routes to generic devices that can synthesize a variety of different radiolabeled probes on demand. Described herein is a novel radiosynthesis platform based on handling of fluids in droplet forms. The unique platform is demonstrated through the use of a technique referred to as electro-wetting-on-dielectric (EWOD) which is a voltage-based actuation method to manipulate liquids.

Particular advantages of EWOD devices for radiochemical synthesis include, but are not limited to the following:

Inert materials. The wetted materials are typically only fluoropolymers (e.g. Cytop™ or Teflon AF™). These materials have high chemical and thermal stability and are expected to be compatible with a wide range of reaction conditions.

Open channels. Open channels permit rapid evaporation of solvents. Evaporation is a frequent operation during $^{18}$F-radiosyntheses, wherein drying of [$^{18}$F]fluoride ion is a usual step, as well as removal of solvent prior to a solvent-exchange operation. The open channels also enhance mixing, which is restricted in other types of microfluidics involving closed channels. Speeding up such operations is important when working with short-lived radioisotopes.

Flexible fluid path. In principle, a single chip design with an "array" of electrodes could perform a wide variety of syntheses simply by reprogramming the droplet movements for different syntheses. The single chip would drive down manufacturing costs, and provide expandability to new probes with only a software change. The flexibility could also be used to implement reaction optimization, study of reaction kinetics, etc.

Liquid diversity. Small volumes of many different types of liquids, including aqueous solutions and organic solvents, can be manipulated within the same EWOD device. (Different electrical signals may be necessary with some liquid combinations.) In channel microfluidics, manipulation of small volumes requires proper matching of liquids and channel surface properties to avoid large losses; thus, to manipulate different solvents in the same device (as is typical for radiochemical reactions) requires specialized fabrication methods, including hybrid devices based on multiple materials and locally treated channel surfaces.

Straightforward fabrication. The EWOD chip is fabricated using known integrated-circuit processing steps. For example, electrodes are patterned using electrically conductive materials, such as indium tin oxide (ITO) or gold on an insulating layer, such as silicon nitride, the structure being covered by a hydrophobic film. Chips can also be made using industry standard printed-circuit-board manufacturing (plus hydrophobic coating). The device simplicity allows many other fabrication options, e.g., screen printing, inkjet printing, and roll-to-roll printing, for a range of different cost and performance. EWOD chips can be mass produced at a lower cost per chip for disposable use.

Simple system. The EWOD device is operated only by using voltage signals, typically below 100 V. A pressure source (e.g., pump), flow regulator (e.g., valve), complex plumbing, moving parts, high voltage (e.g., kV for electrokinetic drive), or high power (e.g., thermal, electromagnetic) are not required. Consisting only of a small printed circuit board, the complete system is small and easy to fit into the hot cell, mini cell, or miniature radiation shielded enclosure.

Small fluid volumes. EWOD devices can reliably manipulate fluid volumes from hundreds of microliters to picoliters. Working at a volume scale below the milliliter volumes of conventional macroscale approaches enables faster processes (heating, evaporation, and cooling, etc.), higher radioisotope concentrations, lower amounts of reagents which are an important source of undesired impurities, etc.

Other advantages include the capability of printing "dried" reagents directly on an EWOD chip. Fresh-solvent droplets are used to redissolve these reagents and use them in the chemical synthesis process. The use of reagents dried on the chip allows the construction of a "kit" for synthesizing a particular probe—this has enormous potential for simplifying probe synthesis, in a highly reliability and reproducible manner by the use of standard reagents of controlled quality.

As described herein, it can now be shown that liquid actuation on EWODs can be accomplished using transport of droplets, merging of droplets, mixing of droplets, or splitting of droplets. Droplets can be dispensed with fixed or controlled volume (via capacitance or other feedback). Further, sensors and actuators can be integrated into chips, for example for liquid detection (monitoring processes) volume measurement, and temperature control (heating and resistance feedback).

BACKGROUND

Microfluidic devices have been used in radiochemistry since about 2004. A recent review by Elizarov (ibid.) summarizes the various approaches that have been taken. It is a common view in the field that the use of microfluidics has many advantages over the predominant macroscopic methods (manual and automated systems) for the production of PET tracers.

In regard to microfluidics, most researchers have used continuous flow microreactors (Elizarov (ibid.)) that still require substantial auxiliary equipment such as syringe pumps, F-18 drying subsystems, etc. As a result, these systems are bulky, complex, and expensive. The few "integrated" approaches (C.-C. Lee, G. Sui, A. Elizarov et al., "Multistep Synthesis of a Radiolabeled Imaging Probe Using Integrated Microfluidics," *Science*, vol. 310, no. 5755, pp. 1793-1796, Dec. 16, 2005) that have been tried suffer from material compatibility problems. For example, PDMS is not compatible with many organic solvents and other reaction conditions used in probe syntheses. Further, very low reliability of operation has been observed. Integrated approaches all use microfluidic devices with well-defined channel patterns. This restricts flexibility and in most cases, requires that different probes use different chip designs.

SUMMARY

Shown herein are improved, unique EWOD devices, reactant delivery systems and processes for preparing radio-compounds using these devices and delivery system.

Disclosed herein are methods of performing microchemical reactions and electro-wetting-on-dielectric devices (EWOD devices) for use in performing those reactions.

The device comprises:
a first substrate having one or more fluid paths on a first surface thereof, each fluid path comprising multiple discrete electrically conductive electrode pads spaced from and insulated from the fluid path, adjacent conductive pads in said fluid path separated from each other by non-conductive spaces, each of the multiple conductive pads having electrically conductive lines attached thereto, each conductive line provided for delivering electrical signal to the conductive pad to which said conductive line is attached to provide electrically directed movement of a fluid droplet along said fluid paths,
one or more fluid delivery sites located on or adjacent the one or more fluid paths, and
one or more reaction sites or heater sites located along the fluid paths on said first substrate,
said fluid paths leading from the one or more fluid delivery points to the one or more reaction sites or heater sites.

The device can also include a second substrate positioned over the first substrate, the second substrate being position parallel to the first substrate with a defined space between the first substrate and the second substrate. The second substrate can be electrically conductive or have an electrically conductive film coating on a surface of the second substrate facing the defined space, said conductive substrate or electrically conductive film coating providing an electrical ground. In one embodiment one or more portions of the first substrate extend beyond one or more edges of the second substrate to provide the one or more fluid delivery sites, the fluid delivery sites being located on or adjacent conductive fluid paths at the one or more edges of the second substrate.

The heater sites can comprise, discrete electrically conductive pads, each discrete electrically conductive pad being independently connected for independent control of the temperature of each heater pad. Further, the one or more heater sites can comprise concentric, discrete electrically conductive pads.

A dielectric layer and a hydrophobic film coating preferably cover at least the conductive pads and conductive lines.

Also disclosed is a fluid delivery device for providing droplets of reactants to the fluid delivery sites comprising:
a sealed container for holding liquid for delivery comprising the chemical in a liquid carrier, said container having means for continuously or periodically delivering a pressurized gas to a head space in the container above the liquid for delivery,
a tube extending upward from a top portion of the sealed container for transferring the chemical in the liquid carrier from the sealed container to a delivery location positioned above the sealed container, and
a source of pressurized gas and means for delivering said pressurized gas to the sealed container in a controlled continuous or periodic manner sufficient to prevent flooding.

Sensing means for detecting that a droplet of the liquid carrier has reached the delivery location or an intended second location, can be provided, said sensing means or a second sensing means also detecting that no more than a desired quantity of the liquid carrier has reached the intended second location.

A procedure for using the above described electro-wetting-on-dielectric device (EWOD) comprises:
placing a droplet comprising a first chemical reactant in a liquid carrier, preferably volatile, at one of the fluid delivery sites, said delivery site being at or spaced from the one or more heater sites,
if the droplet is placed at a delivery site spaced from the heater site, providing an electric field in a serial manner to the adjacent conductive pads spaced from said fluid path to move the droplet from the fluid delivery point to a heater site,
placing a droplet of a second chemical reactant in a liquid carrier, preferably volatile at one of the fluid delivery sites,
providing an electric field in a serial manner to the adjacent conductive blocks spaced from said fluid path to move the droplet of the second reactant from the fluid delivery point to the heater site, and
heating the combined first and second reactants to cause a chemical reaction between said first and second reactants to form a desired intermediate or end product, and
further reacting or recovering the desired intermediate or end product.

The droplet of the first reactant is heated at the heater site to partially or fully remove the liquid carrier by evaporation before adding the droplet of the second chemical reactant. Additional droplets of the first reactant or the liquid carrier can then be transported to the heater site before addition of the droplet of the second chemical reactant, said additional droplets of the first reactant being transported to the heater either before evaporation, after partial evaporation or after completing evaporation of prior delivered droplets of the first reactant. The droplet of a second chemical reactant in a liquid carrier is then combined with the first reactant on the heater site either before evaporation, after partial evaporation or after completing evaporation of prior delivered droplets of the first reactant. The first reactant in combination with the droplet or droplets of the second reactants are then heated for a sufficient period of time to react to provide the desired intermediate or end product.

Additional volatile liquid carrier can be transported to the heater site during the reaction to maintain the first and second reactants in a liquid environment, partial or total evaporation being effected after sufficient time has elapsed to complete the desired reaction. As an alternative, more than two reactants can be delivered to the heater site for preparing an end product.

In one alternative embodiment a droplet of a mixture of chemical reactants in a liquid carrier is placed at one of the fluid delivery sites. The droplet is then moved to a heater site and is heated to cause the desired reaction to produce the intended intermediate or end product, and remove the volatile liquid carrier.

The above described devices and method are particularly suited for preparing radiochemical compounds, particularly compounds containing $^{18}$F.

DESCRIPTION OF FIGURES

FIGS. 3-5 are schematic diagrams of three different heater embodiments.

FIG. 6 is a schematic drawing showing an embodiment of an EWOD chip with two liquid feeds.

FIG. 7 is a schematic drawing similar to FIG. 6 also showing the electrical leads and connection sites.

DETAILED DESCRIPTION

Figure 1:
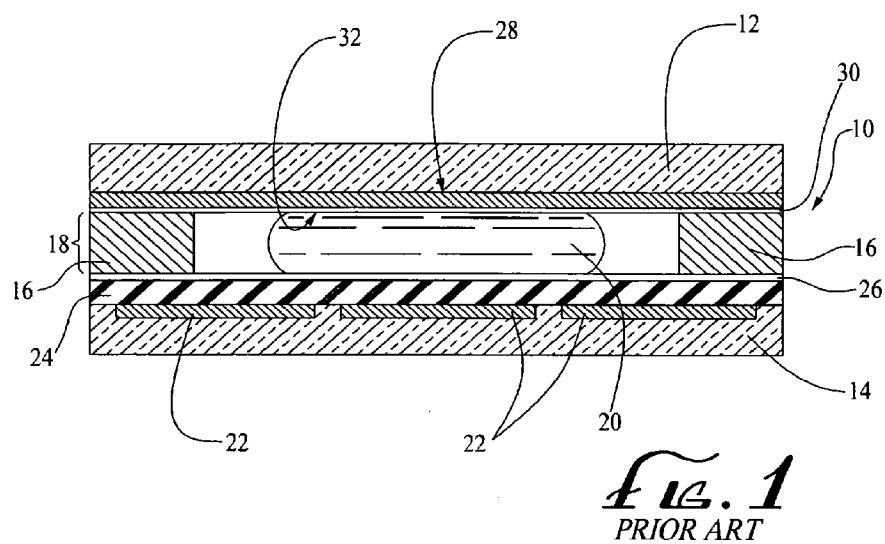
FIG. 1 is a schematic diagram showing an embodiment of an EWOD chip with stacked components.

The structure of an EWOD chip 10 is shown in FIG. 1. The operation of EWOD devices and the driving of fluids across the surface of these devices is described in Shih-Kang Fan, Peter Patrick deGuzman, Chang-Jin Kim, "EWOD Driving of Droplet on N×M Grid Using Single Layer Electrode Patterns", Solid-State Sensor, Actuator and Microsystems Workshop, Hilton Head Island, S.C., Jun. 2-6, 2002, said article incorporated in its entirety by reference herein. In a preferred embodiment, two glass substrates 12, 14 (a top plate and a bottom plate) are held together in a spaced apart orientation with a 100 μm spacer 16 (i.e., double-sided tape) to form a gap 18 for placement of liquid droplets 20 (small drops of a liquid). The bottom-plate substrate 14 has control electrodes 22, usually comprising ITO or gold, formed or positioned on the top surface thereof. An insulating dielectric layer (such as silicon nitride) 24, located over the control electrode 22 is covered by a hydrophobic film layer 26, such as a Cytop® or Teflon® film. The bottom surface of the top-plate substrate 12 is covered by a conductive film 28, such as ITO, which functions as a ground electrode. However, in alternative embodiments the second substrate can be eliminated, providing an open structure with the droplet resting on the first substrate upper surface. In such an instance the ground electrode can be located in a different location, for example below or within the first substrate. In the two substrate structure, a layer of an insulating dielectric 30 (such as silicon nitride), which is preferably thinner than the insulating dielectric 24 on the bottom plate, preferably one-tenth the area of the lower plate insulating dielectric 24, covers the ground electrode 28. A hydrophobic layer 32 covers the lower face of the upper dielectric 30. EWOD chips can be formed using various known techniques including but not limited to standard chip formation technology using printed circuit board fabrication techniques or flexible electronics.

Preferentially, the EWOD chip 10 is transparent except for the electrical connection pads 41 along two edges of the chip and several conductive (preferably gold) connection lines 52 connected to the control electrode pathways 42 leading to the heater 44. Droplets 20 of water, DMSO, MeCN, or other liquid carriers are transported into and along the gap 18 between the two substrates 12, 14 along the pathways 42 by voltage signals applied to the connection pads 41 and through the conductive connection lines 52.

Figure 2:
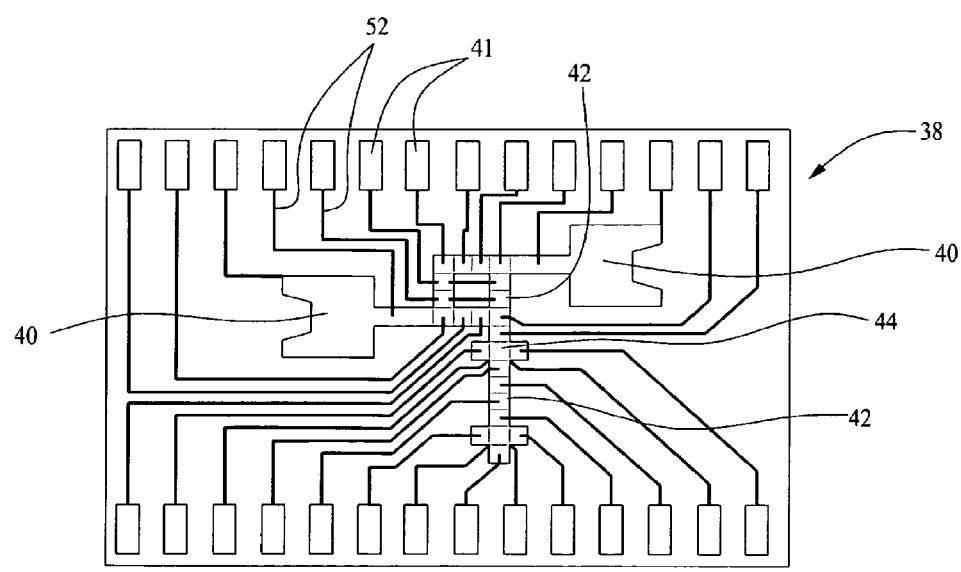
FIG. 2 is a schematic drawing showing the control electrode pattern of an EWOD chip incorporating features of the invention.
Figure 8:
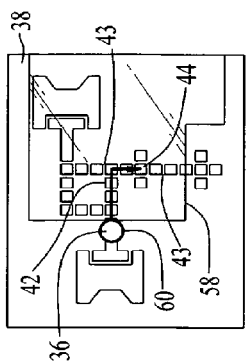
FIGS. 8-16 are schematic diagrams of nine successive steps in the uses of an EWOD chip incorporating features of the invention.
Figure 9:
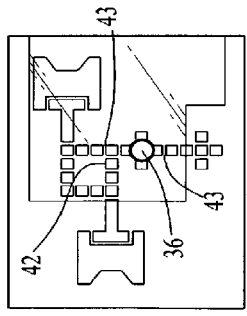
Figure 10:
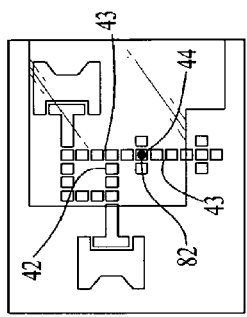
Figure 11:
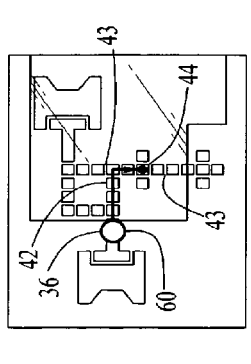
Figure 12:
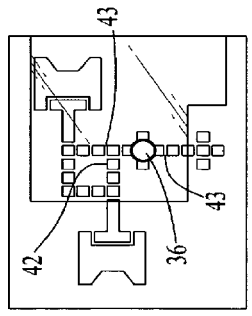
Figure 13:
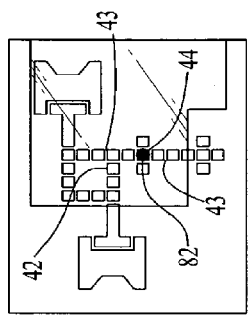
Figure 14:
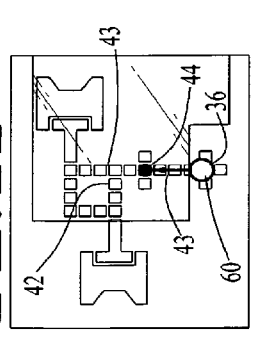
Figure 15:
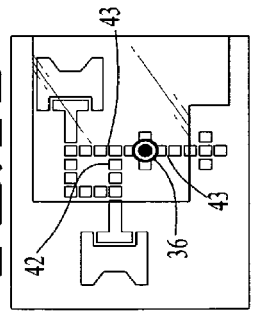

An electrode pattern of an EWOD chip design 38 incorporating features of the invention is shown in FIG. 2. Located within the pattern are two reservoirs 40 which may receive the solutions involved in the reaction. The electrical connection pads 41 are connected by conductive connection lines 52 to the conductive pathways 42 (also shown as control electrodes 22 in FIG. 1). The conductive pathways 42 comprise a series of discrete electrically conductive pads separated by non-conductive spaces 43, as best shown in FIGS. 6 and 8-16, below the surface of the chip. In the example shown in the figures, 1 mm×1 mm squares of ITO. The centrally located square is a heater 44. FIGS. 3, 4 and 5 show three alternative heater 44 designs. FIG. 3 is a simple heater electrode design 46 provided to heat the solution droplet placed on the electrode 44. FIGS. 4 and 5 are first and second versions of a self-centering heating electrodes 48, 50, which heat the droplet 20 centered on the heater. Shown at the bottom corners of the heater area are a ground lead 54 and a voltage lead 56 that are connected to a power supply (not shown).

Figure 27:
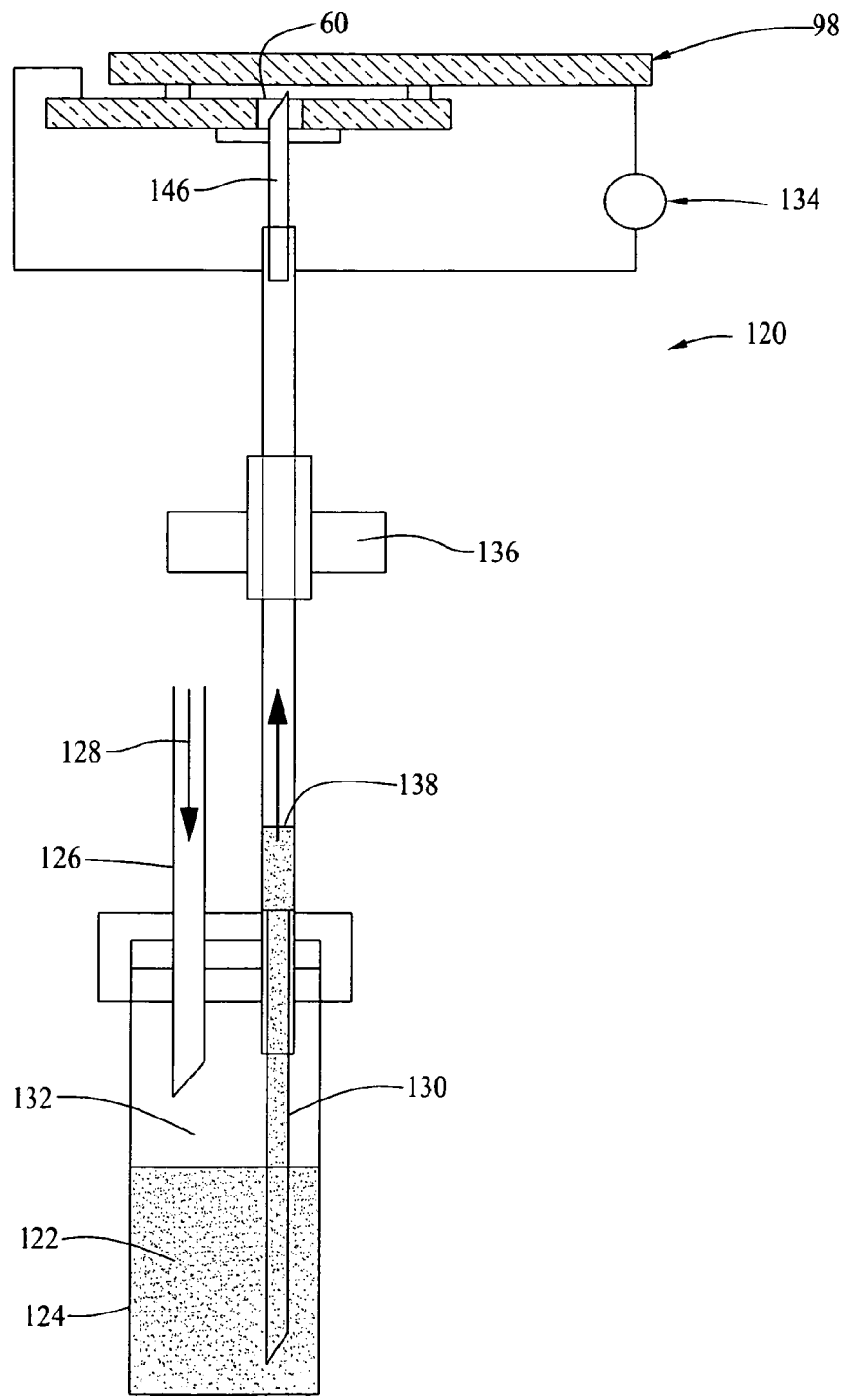
FIG. 27 is a schematic drawing of a pneumatic delivery system.
Figure 28:
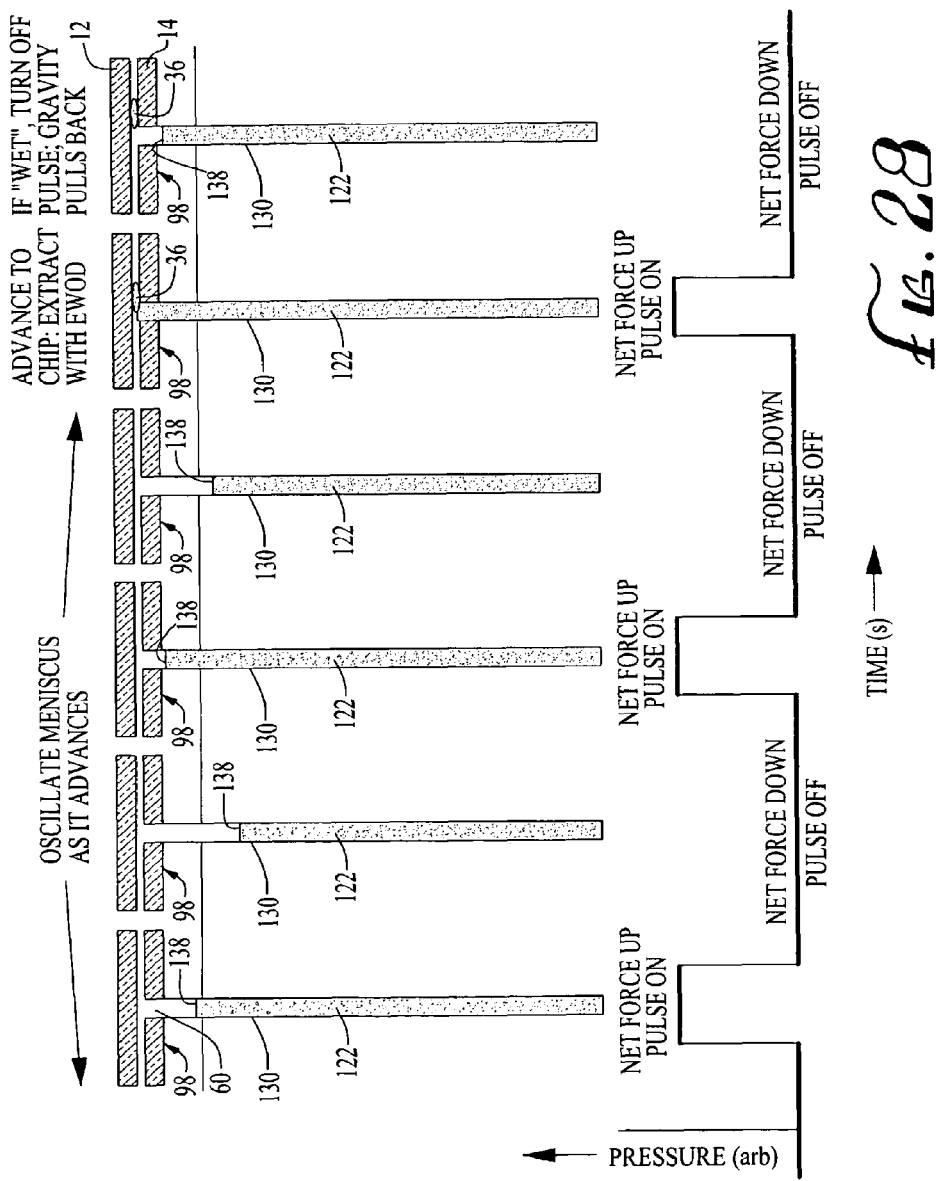
FIG. 28 is a schematic diagram illustrating the positioning of fluid in a delivery tube using the system of FIG. 27.
Figure 34:
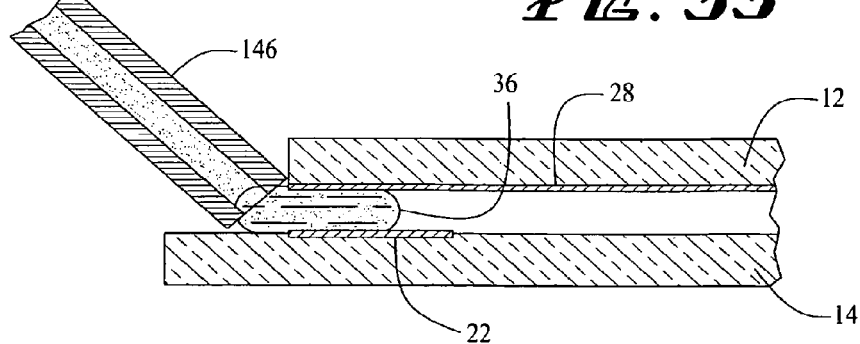
FIG. 34 is a schematic diagram showing pipette delivery of a droplet to a loading position on the EWOD.

FIG. 6 is a schematic drawing showing an embodiment in which a cover plate 58 covers only a portion of the EWOD chip 38. FIG. 7 is another view of the chip shown in FIG. 6 also showing the connection pads 41 and conductive connection lines 52. The incomplete coverage of the chip 38 by the cover plate 58 creates edges preferably near at least one reservoir 40 so that reagents can be loaded into the gap 18 using a pipet or injection needle 146 onto the EWOD chip (see FIG. 34). The embodiment of FIGS. 6 and 7 shows two possible edge loading positions 60 which permit separation of an aqueous reagent (for example an F-18 solution) from an anhydrous solution (precursor solution) by using different pathways on the chip, thus avoiding cross-contamination due to residue that is potentially left behind after droplet motion. Alternatively, the loading positions 60 can comprise holes formed through one of the substrates 12, 14 as shown in FIGS. 27 and 28.

Each connection pad 41 of an EWOD chip is supplied a DC or AC signal (e.g. frequency (~10 KHz) and voltage (~100V)). By applying voltages to various different connection pads 41 in sequence along the edge of the chip, droplets 36 deposited at the loading positions 60 can be caused to move along pathways 42 along the chip surface. Instruments used to move the droplet include a signal generator, high voltage amplifier, digital I/O control box, a relay array and a source meter to supply power to the heating electrodes 48, 50 and to measure the temperature. These commercially-available or custom instruments can be controlled by manually or by software such as LabView software. One skilled in the art will recognize that more than 2 reservoirs 40 and loading positions 60 can be provided on the chip to provide delivery of 3 or more reactants through different pathways 42.

Embodiments and features of EWOD devices incorporating features of the invention that have been built and tested by applicant have included the following:
  Movability of solvents relevant to $^{18}$F-radiochemistry
  Ability to evaporate droplets of water or acetonitrile (also mixtures containing $K_2CO_3$ and K.2.2.2)
  Redissolving the residue left on the heater after solvent evaporation
  Performing reactions at elevated temperatures in volatile solvents
  Cold synthesis of fluoronitrobenzene (evaluated with TLC)
  Hot synthesis of [$^{18}$F]fluoronitrobenzene (evaluated with radio-TLC)
  Hot synthesis of [$^{18}$F]fluorodeoxyglucose (evaluated with radio-TLC)
  Synthesis of 1-(4-bromobutoxy) nophthalene While frequency and voltage may vary depending on device configurations, preferred minimal frequency and voltage of the power supply for manipulating droplets of relevant solutions on the EWOD chip for a particular configuration are shown in Table 1. $K_2CO_3$ solution (similar to composition of [$^{18}$F]fluoride after elution from anion exchange resin) MeCN, DMF and DMSO (in which precursors of many reactions is dissolved) are preferred carrier liquids.

TABLE 1

Minimal frequency and voltage for liquid manipulation

| Solution | Frequency(KHz) | Voltage(V) |
|---|---|---|
| DMSO | 15 | 90 |
| DMF | 20 | 82 |
| Methanol | 5 | 77.3 |
| THF | 15 | 70 |
| K2CO3 | 1 | 75 |

Figure 17:
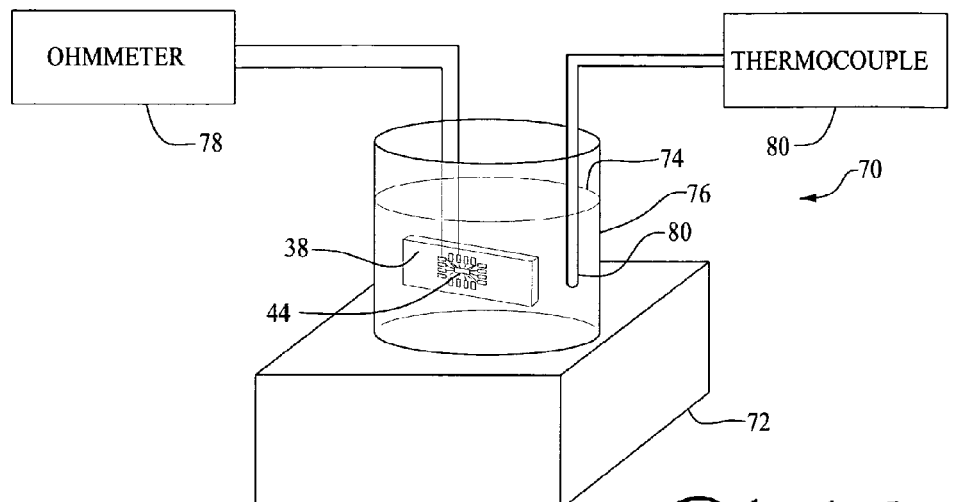
FIG. 17 illustrates a temperature calibration system used to calibrate the heater electrode designs of FIGS. 3-5.
Figure 18:
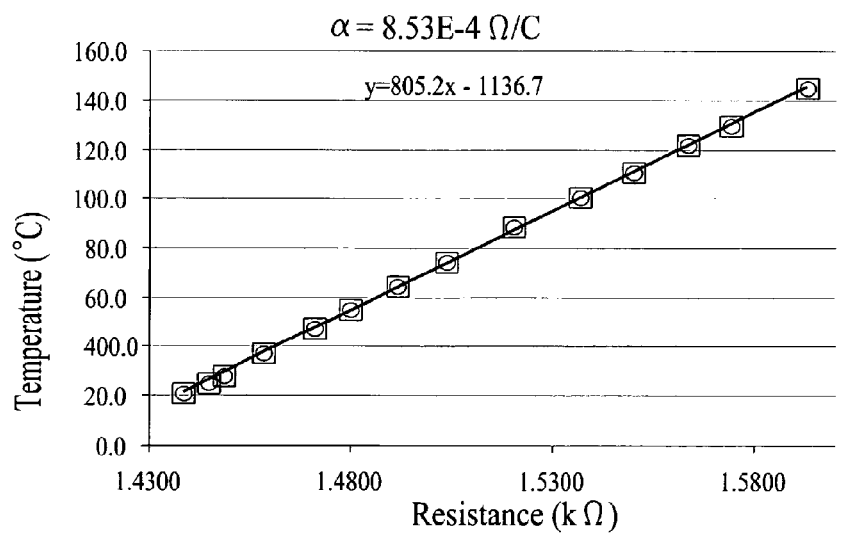
FIG. 18 is a calibration curve for a particular heater design generated using the temperature calibration system of FIG. 17.

Several designs for heaters 44 were fabricated and tested. As a first step, each electrode design was calibrated by immersion in an oil bath. FIG. 17 illustrates a calibration system 70 comprising a hot plate 72 that heats the silicone oil 74 contained in a vessel 76. The resistance of the heater 44 is measured with an ohmmeter 78 and oil temperature (assumed to be same as immersed EWOD device temperature) is measured using a thermocouple 80. Resistance is a function of temperature in accordance with the formula $R=R_o[1+\alpha(T-T_o)]$, where R is resistance at temperature T, $R_o$ is resistance at temperature $T_o$, and $\alpha$ is the temperature coefficient of resistance. The temperature coefficient of resistance for ITO on the EWOD chip is determined by plotting T vs. R and finding the slope of its linear fit (FIG. 18).

With a known temperature coefficient of resistance for the deposited ITO, the temperature of heater 44 can be controlled on the EWOD chip 38. AC or DC current can be applied through positive and negative leads attached to the resistor (heater 44) to heat it, while its resistance is measured. When the calculated resistance for a desired temperature is met, that temperature is presumed to have been reached. The temperature is maintained at the desired set point by software PID control over the control circuit.

The heater 44, the EWOD control electrodes 22 comprising the conductive pathway 42 and EWOD connection lines 52 on a preferred embodiment of the EWOD chip are made of ITO. However, the connection line from the control circuit (not shown) to the heating electrode 44 is made from gold to prevent the connection line from heating when current is applied because gold is a much better conductor than ITO. The heater 44 can reach temperatures greater than 200° C. without damage, but the hydrophobic layers should not be heated above about 190° C.

To test evaporation using the above described embodiment about 400 nL of 1M $K_2CO_3$ solution was transported, using the techniques described herein, to the heater 44 location and the temperature was raised to 105° C. The majority of the solvent was evaporated within 2 min. For lower boiling point solutions (e.g. solutions with lower salt concentration, or solutions containing low-boiling-point organic solvents), evaporation time is substantially lower.

EXAMPLE 1

Demonstration of Non-Radioactive ("Cold") Synthesis

Figure 20:
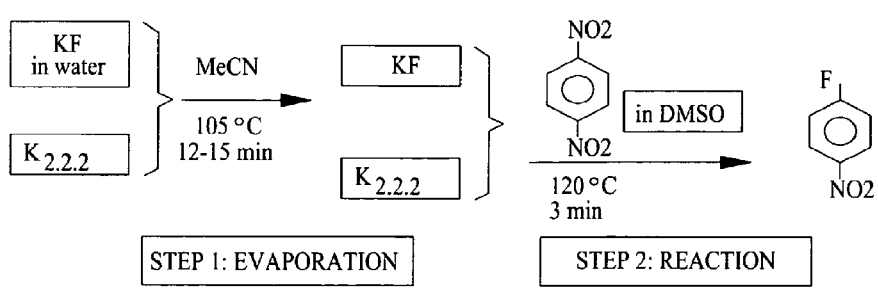
FIG. 20 is the chemical reaction used in the cold run example.

To demonstrate the basic capability for synthesis, non-radioactive fluoronitrobenzene was synthesized on the EWOD chip. This synthesis process on the EWOD chip is shown schematically in FIGS. 8-16 and the chemical reaction is shown in FIG. 20. As the reaction of fluoride with the precursor of 1,4-dinitrobenzene is sensitive to water, this cold run procedure effectively tests the completeness of water evaporation. The product solution can then be separated by TLC and detected with UV light. In the following description "SM" means "starting material" (unreacted precursor) and "P" means the sample of the product.

Two solutions were prepared to perform this reaction.
Solution 1 (Fluoride solution) was 115 mM KF+234 mM Kryptofix K.2.2.2 in a solution of acetonitrile (MeCN) and water (88:12 v/v ratio), and
Solution 2 (Precursor solution) was 119 mM 1,4-dinitrobenzene in DMSO.

Figure 16:
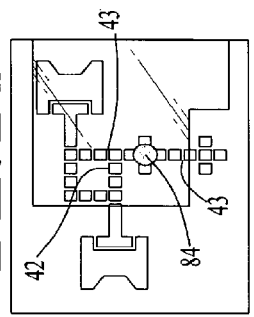
Figures 19A, 19B, 19C, 19D:
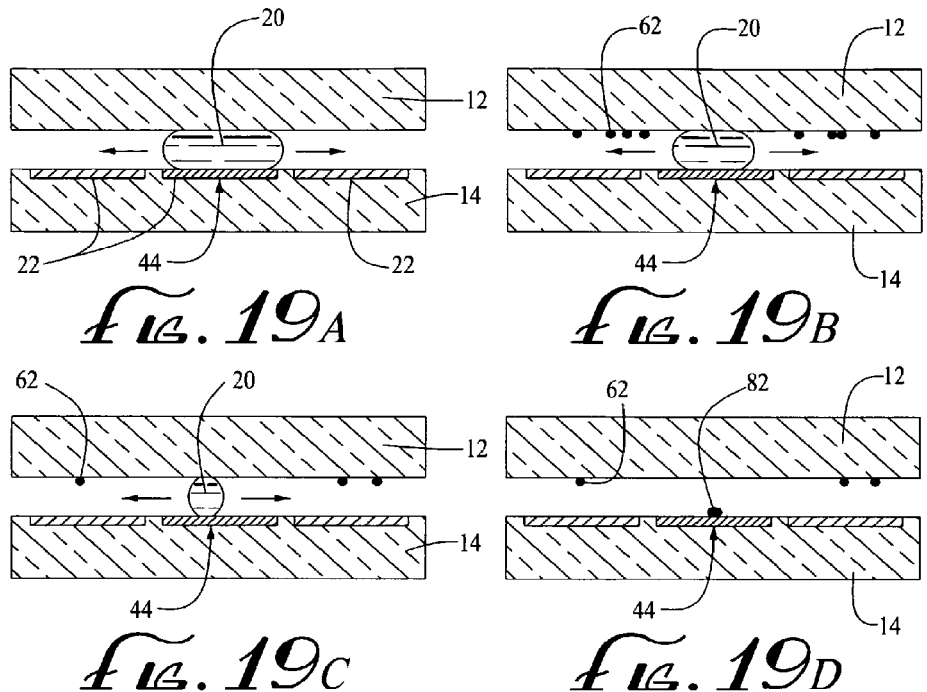
FIGS. 19 A-D show a series of stages in the evaporation of a droplet.

Referring to FIGS. 8-16 and 34, reagent droplets 36 were loaded onto the EWOD chip 38 at the loading position 60 along the edge of the cover plate 58 using a pipette (FIG. 8) The EWOD chip electrodes then transported the droplet along the pathway 42 to the heater 44 (FIGS. 8-9) where it was heated and the liquid evaporated. More particularly, the procedure using the EWOD chip is as follows:

1. 500 nL of a first solution was placed at the edge inlet 60 and transported to the heater 44
2. The heater 44 was heated to 105° C. for 3 minutes. (FIG. 10) leaving a dried residue 82 on the heater location
3. 600 nL of MeCN was loaded at edge inlet 60 (FIG. 11) and transported to the heating electrode 44 (FIG. 12).
4. The MeCN was then heated at 105° C. using the heater for 3 minutes (FIG. 13) to evaporate the MeCN to help remove residual water from the residue 82. FIG. 19A schematically shows the droplet located at the heater 44 position, the arrows representing the release of vaporized liquid carrier. FIG. 19B shows partial condensation 62 of the vapor on the bottom of the upper plate 12. FIG. 19C shows dissipation of the condensed droplets as the lower surface gets warmer as a result of heat from the heater. FIG. 19d shows complete or substantially total evaporation of the liquid from the droplet, leaving behind the dried solute residue 82 of [$^{18}$F] compound
5. Step 3 and step 4 were repeated several times. (This process is called azeotropic distillation and its purpose is to remove as much residual water as possible due to water-sensitivity of fluorination reaction.) A positive correlation was observed between the number of times steps 3-4 are repeated and the end product yields.
6. 500 nL of a second solution (precursor) was then loaded at the second edge inlet 60 (FIG. 14) and transported to the heating electrode 44. (FIG. 15).
7. The combination of dried, water free first solution residue and precursor were then heated to 120° C. using the heater for 3 minutes to react the two materials, generating the desired reaction end product 84. (FIG. 16).

After the evaporation and reaction, the top-substrate and bottom-substrate of the EWOD chip were separated. The product was removed using a capillary, and then TLC separation and UV light detection was performed with buffer dichloromethane and hexane (1:1 v/v). Through comparison of a sample of the product of on-chip reaction, along with "standards" (precursor and a "cold standard" of the known final product) the proportion of desired product and unreacted precursor was estimated to provide an estimate of the reaction yield.

EXAMPLE 2

Radiosyntheses ("Hot" Runs)

A corresponding hot run, i.e. radiosynthesis of [$^{18}$F]fluoronitrobenzene ([$^{18}$F]FNB) was also conducted. The hot run reaction procedure was similar to the cold run, except using [$^{18}$F]fluoride produced in a acyclotron rather than KF solution. No-carrier-added [$^{18}$F]fluoride ion was produced by 11 MeV proton bombardment of 98% enriched [$^{18}$O]water in a silver target body using a RDS-112 cyclotron. Two reagent solutions were prepared:
Solution 1 (F-18 solution) contains 55 mM K$_2$CO$_3$, 112 mM Kryptofix K.2.2.2, and 58 nM F-18 in a mixture of MeCN and water in the ratio 84:16 (v/v);
Solution 2 (precursor solution) contains 119 mM 1,4-dinitrobenzene in DMSO.

Figure 21:
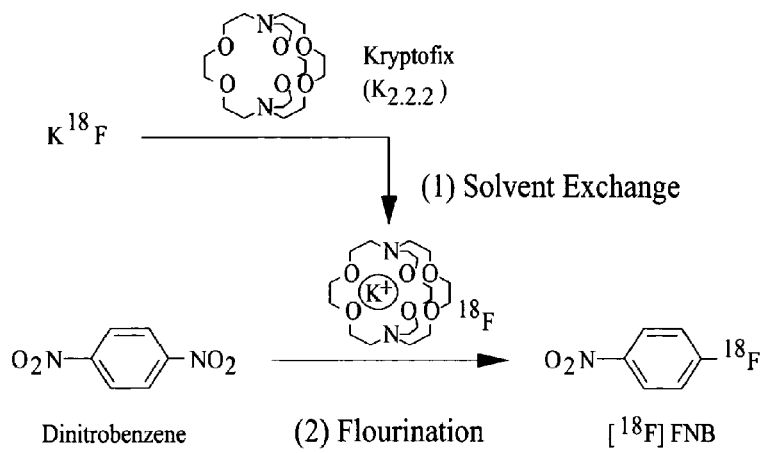
FIG. 21 shows the chemical reaction used in the hot run example to prepare [$^{18}$F]FNB.

As is typical of $^{18}$F-radiosyntheses using [$^{18}$F]fluoride, an important step was drying and activating the F-18 after its elution from ion exchange cartridge. Reaction of the K$^{18}$F/K$_{2.2.2}$ with the precursor (1,4-dinitrobenzene, typically in DMSO) then yields the product 1-[$^{18}$F]fluoro,4-nitrobenzene. The chemical reaction is shown in FIG. 21. The detailed steps of the hot run were identical to that for the cold run.

Solution 1 was deposited at the loading position on the chip, transported to the heater location and evaporated and solution 2 was then brought to the same location. Following the synthesis, the product was separate by silica gel TLC (buffer MeCN/H2O 95:5 v/v) and visualized with a radio-TLC scanner to determine the relatively amounts of radioactive species and thus the reaction yield.

Figure 22:
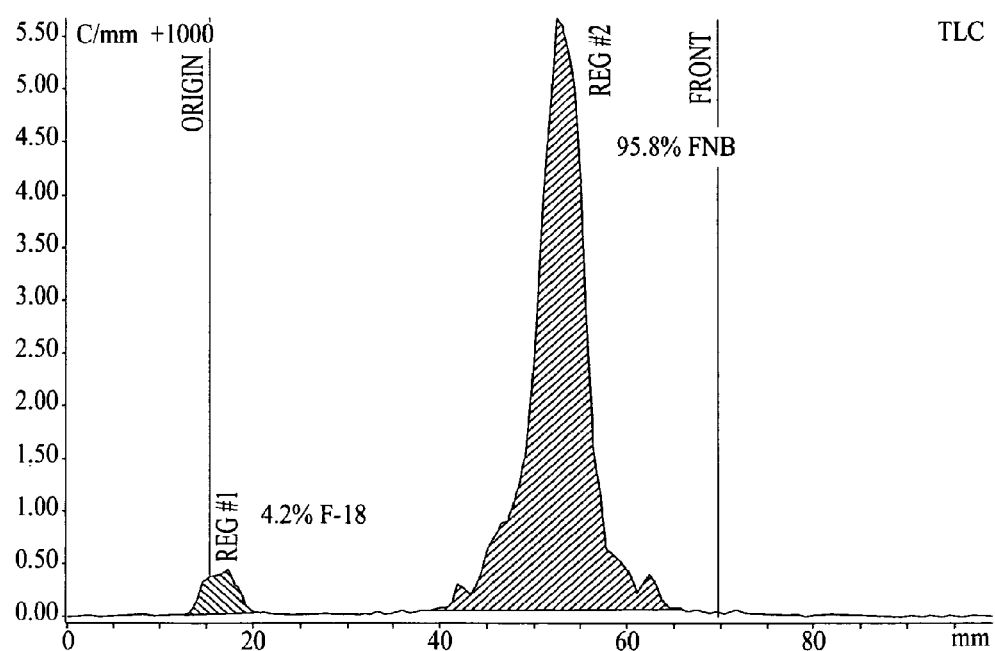
FIG. 22 is the TLC graph of the product from the hot run ([$^{18}$F]FNB production)

See FIG. 22 for the TLC profile.

Using the radio-TLC profile, the area of each peak is integrated. From studies of "standards" it is known at which positions different chemicals will remain under the conditions used for separation. In the example of FIG. 22, the first (left) peak corresponds to unreacted [$^{18}$F]fluoride. The second (right) peak corresponds to the desired product. The TLC result shown in FIG. 22 indicates that the conversion efficiency (from F-18 to desired product [$^{18}$F]fluoronitrobenzene) was about 96% Conversion was consistently high for several runs with an average conversion efficiency of 78%±12% (n=8 runs), consistent with conventional synthesis of this compound. The sample recovery was about 29% as discussed above. Thus radiochemical yield (RCY) of [$^{18}$F]fluronitrobenzene from [$^{18}$F]fluoride in the EWOD chip is calculated to be 96%×29% (i.e., 28%). Varying operating conditions and handling of the materials has since resulted in far lower losses with recoveries in the range 80-100%.

Figure 35:
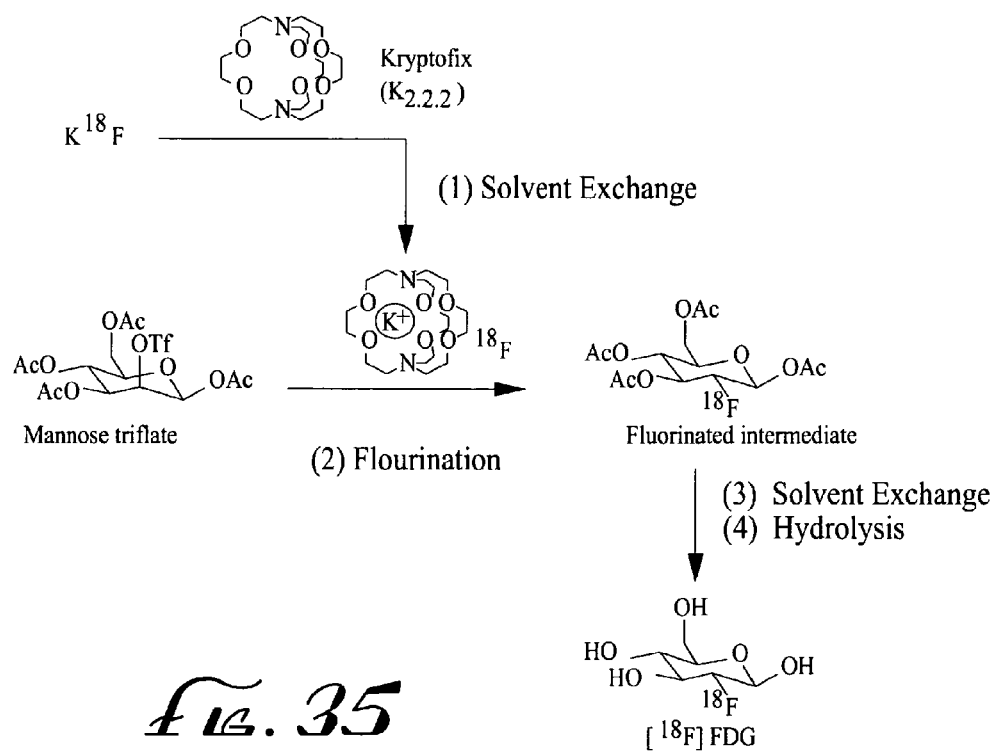
FIG. 35 shows the chemical reaction used in the hot run example to prepare [$^{18}$F]FDG.

A hot run was also performed to produce $^{18}$F-labeled fluorodeoxyglucose ([$^{18}$F]FDG). According to the reaction scheme shown in FIG. 35. The hot run procedure for [$^{18}$F] FDG is similar to that for [$^{18}$F]fluoronitrobenzene, with a few differences. The main difference is that [$^{18}$F]FDG requires a second reaction, a hydrolysis step—to remove acetyl protecting groups from the fluorinated intermediate. Also, the nucleophilic substitution of $^{18}$F onto the precursor occurs in the solvent MeCN instead of DMSO.

Reaction of the K$^{18}$F/K2.2.2 activated complex with precursor mannose triflate (typically in MeCN) yields the intermediate [$^{18}$F]FTAG. The MeCN is then evaporated and replaced by HCl for hydrolysis to form the final product, [$^{18}$F]FDG.

Three solutions were prepared:
Solution 1 (F-18 solution) contains 55 mM K$_2$CO$_3$, 113 mM Kryptofix K.2.2.2 and about 26 nM [$^{18}$F]fluoride in a mixture of MeCN and water (84:16 v/v).
Solution 2 (precursor solution) contains 114 mM mannose triflate in MeCN.
Solution 3 (deprotection solution) contains 1N HCl.

For radiosynthesis of [$^{18}$F]FDG, a 500 nL droplet of Solution 1 was loaded onto the EWOD chip and moved to the heater site, where it was heated at 110° C. for 3 minutes leaving a residue. An azeotropic drying step was then repeated several times (generally 3-5; however, as many as 10 repeats have been used). The azeotropic drying step consisted of loading a 600 nL droplet of MeCN onto the chip, moving it to the heater to dissolve residue remaining from the previous step, and drying at 110° C. for 3 minutes. Once drying of the fluoride was complete, a 900 nL droplet of Solution 2 was loaded onto the chip and moved to the heater site. Heating at 85° C. for 5 minutes formed the [$^{18}$F]FTAG intermediate. Because MeCN has a low vapor pressure and rapidly evaporates during the reaction, 600 nL droplets of MeCN were added every 30 seconds and moved to the heater to ensure a liquid-state reaction. The [$^{18}$F]FTAG droplet was dried (MeCN evaporated) by heating it to 95° C. for 1 min. 1 μL of HCl (1 M) was loaded, moved to the [$^{18}$F]FTAG site, and heated at 95° C. for 3 minutes to perform hydrolysis for the removal of a protective acetyl group and form [$^{18}$F]FDG.

The sample was recovered from the EWOD chip and separated by silica TLC, MeCN and water (95:5 v/v). The resultant separated materials were measured with a radio TLC reader (FIG. 23).

Figure 23:
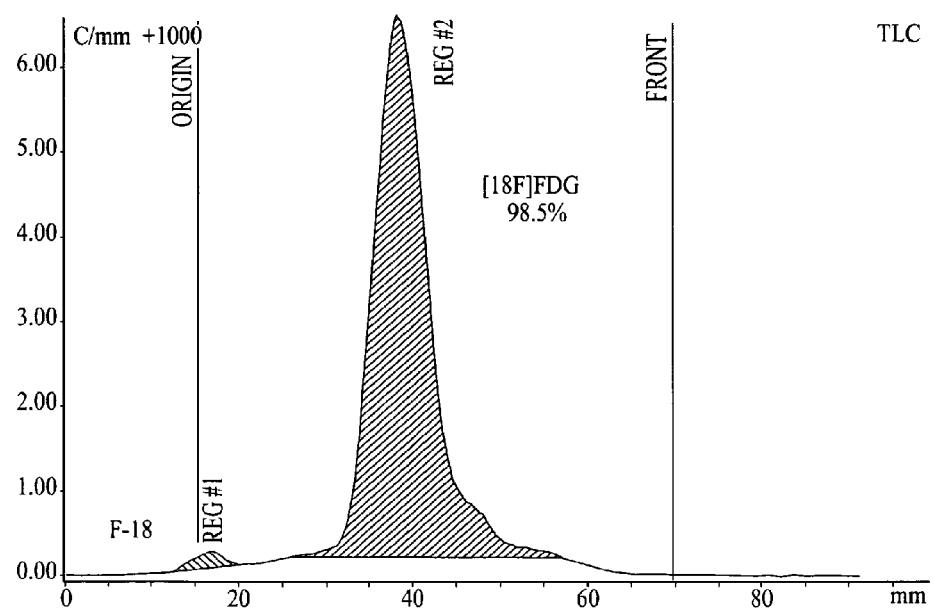
FIG. 23 is the TLC graph showing the results of [$^{18}$F]FDG production.
Figure 24:
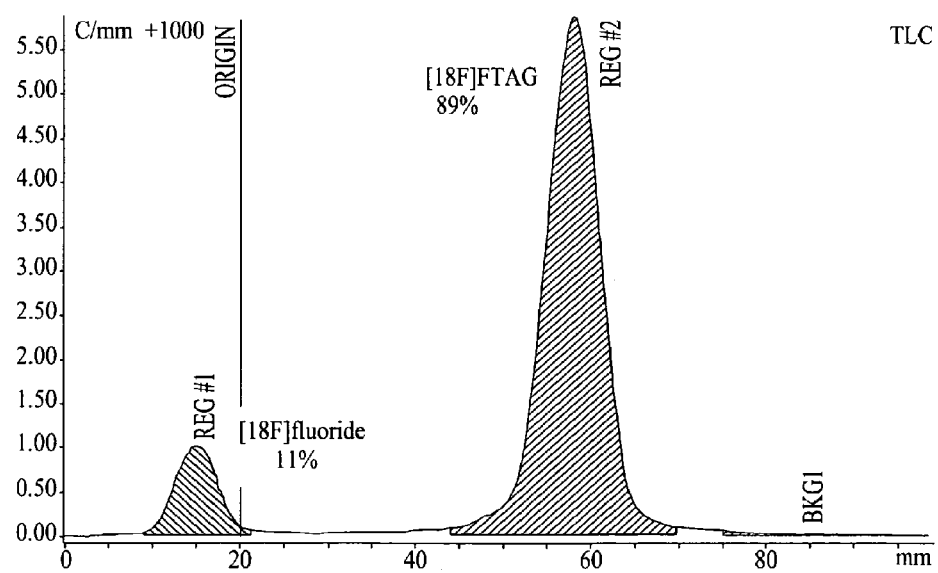
FIG. 24 is the TLC graph showing the results of [$^{18}$F]TAG production.

FIG. 23 shows the composition of a sample recovered by dissolving into a water solution of [$^{18}$F]FDG synthesized on the EWOD chip. Radiochemically, it is primarily FDG. FIG. 24 shows the composition of a sample recovered by dissolving into a MeOH solution of [$^{18}$F]FTAG synthesized on the EWOD chip.

Several repetitions of [$^{18}$F]fluoronitrobenzene synthesis and [$^{18}$F]FDG synthesis have been performed with high repeatability. Synthesis of additional relevant probes, includes [18F]fluoro-3'-Deoxy-3'-L-fluorothymidine [$^{18}$F] FLT, 9-[4-[18F]fluoro-3-(hydroxymethyl)butyl]guanine [$^{18}$F]FHBG, and 3,4-dihydroxy-6-[18F]fluoro-L-phenylalanine [$^{18}$F]FDOPA Alternative approaches within the scope of the invention include:
A microfluidic chip (e.g. PDMS) to deliver small reagent volumes
A robotic pipetting system
Connection of tubing-to-the EWOD interface for delivery of reagents
Automated methods to recover the final product
Holes through the chip cover plate for use as loading positions
Use of tubing, pipette, or vacuum to recover liquid
A standalone "radiosynthesizer" based on an EWOD chip, complete with reagent loading system, product collection system, monitoring system, control system, and radiation shielding.
Design of computer-controlled system for simple reaction optimization/exploration (including varying temperature, concentrations, mixing ratio, reaction time, etc. . . . )
Integration of EWOD chip with radioactivity camera to study surface adsorption and track fate of all radioactivity on the chip (to determine yields, and losses that can be optimized)
Added channels inside the EWOD chip in select locations.
Limitation or prevention of evaporation to allow storage of chemicals in reservoirs on the chip.
Isolation of water vapor from dry organic solvents on chip
Walls on the chip to help with elution off of soiled electrodes (e.g. with gas or liquid)
Inclusion of Argon or Helium filled chambers to protect air or water-sensitive reagents
On-chip storage of dried reagents. This may include depositing liquid reagents, drying them (evaporation), or reconstituting at time of synthesis by addition of droplets of pure solvents. By having reagent pre-loaded, the chip will be much easier to use by individuals not trained in radiochemistry.

In the designs above, 1 mm by 1 mm square resistive elements were used for heating droplets to evaporation and reaction temperatures. With a gap of 100 μm (approximately 0.2 mm) between the cover plate and chip, the nominal droplet volume of about 100 nL allows processing of up to several hundred nanoliter droplets. At this length and volume scale, feedback control using simple measurements of the average temperature over the whole resistive element can maintain a controlled temperature distribution over the small area resistors. However, the small area limited the reaction volume and amount of starting material that could be processed.

While the above examples describe the delivery of first and second droplets of two reactants, it is also contemplated that the first and second reactants can be mixed together prior to delivery and then a droplet of the combined reactants can be placed at the delivery site for movement to the heater, or placed directly on the heater where the reaction is performed. As a further alternative droplets of additional reactants can be placed and moved to the same heater site for use in the chemical reaction.

Figure 25:
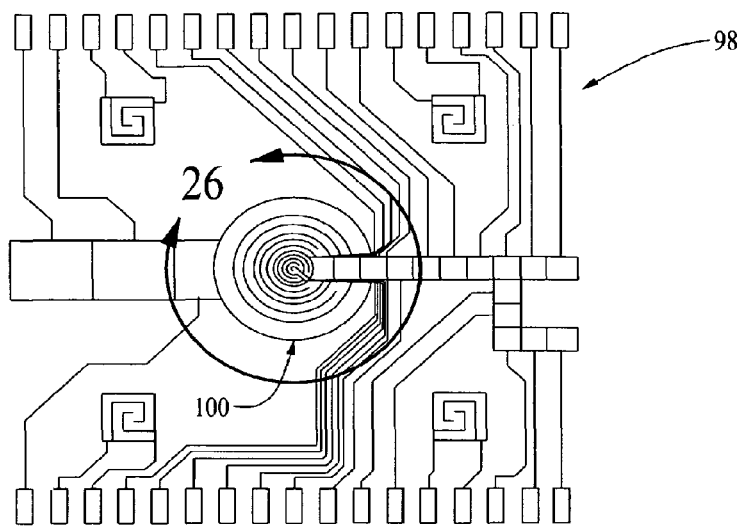
FIG. 25 is a schematic diagram showing a second EWOD design.

The use of an EWOD chip 98 incorporating larger circular heaters 100 having 12 mm overall diameter such as shown in the further chip embodiment shown in FIG. 25, and in the enlarged view of the heater 100 enclosed in the circle 26 of FIG. 25 (FIG. 26), a larger amount of product can be generated with each heater 100 (approximately 23 μL). In order to avoid disparate hot and cold regions when only the average temperature over the entire large heating area remains controlled, the heater is divided into 4 concentric resistive elements 102, 104, 106, 108, each with its own feedback control of temperature (not shown). Compared to the first described heater design 44, such as described above, this multi-element heater can center the droplet and maintain its temperature more uniformly as the droplet shrinks during evaporation.

The larger size of the heater 100 enables processing to produce larger amounts of tracers. Also, when using volatile solvents, the larger volumes slightly prolongs the droplet lifetime at a given temperature, thereby allowing longer duration reactions, or requiring less frequent replenishment of the evaporating solvent.

A multichannel heater controller and driver (not shown) provides an expandable platform for achieving and maintaining multiple, independent EWOD reaction sites at precise temperatures. The instrument was specifically designed for the resistive micro-heaters patterned on the EWOD chip. It incorporates a low noise, real-time, zero resistance current measurement and amplification while providing a self-powered, amplified heater driver with parameters which can be controlled by dedicated software. The platform enables parallel reactions at independent temperatures on the same or separate EWOD chip as well precise spatially varying temperature profiles for a single reaction site, when used in conjunction with concentric heaters 100 or resistive elements patterned in close spatial proximity.

The first embodiment discussed above used an expensive source meter to provide the measurements for feedback control. Advantages of the temperature control circuit in the second EWOD embodiment 98 include:
No measurement interference with the heater electrodes on the EWOD chip. The system introduces negligible resistance and current while making measurement
The system can make measurements and control multiple heated reaction sites independently The system allows high speed measurement and control The system provides amplification to interface with readily available data-acquisition systems for precision temperature control and measurement The software is designed to calibrate a new chip, by making automatic initial measurements, such as resistances at room temperature and making adjustments for offset currents The software incorporates digital low-pass filters and can make measurements at up to 20,000 samples/sec from each independent heater to achieve near real-time measurement and control to provide further stability by averaging Circuit size and cost are small Preferred operating conditions for loading fluid solutions containing samples, reagents, catalysts etc. onto the chip for EWOD-based radiochemistry system are:

Delivery of small droplet volumes (typically 0.1 to 2 μL)

Delivering reagents rapidly and frequently to EWOD chip (e.g. to replenish evaporating solvents)

Compatibility with wide variety of reagents (solvents, corrosive agents, etc.) over long time periods (e.g. so that reagents could be supplied in a "kit")

Disposability to avoid the need for washing to eliminate cross-contamination, and to enable rapid removal and setup of reagent kits for ease of use Referring to FIG. 27, a pneumatically-driven fluidic loading system 120 is shown. It utilizes inexpensive/disposable components in contact with the reagents, while the more expensive actuating components such as valves, pressure regulators etc. do not contact the reagents. This pneumatically driven fluidic actuation is used for loading liquids into the microfluidic system. In one embodiment, fluid (liquid reagent) 122 is delivered from a supply vessel 124, such as a sealed chamber (e.g. vial). Two tubes are inserted into the vial. A first tube 126 is used for delivering an inert gas 128 to the space above the liquid; the second tube 130, which has one end immersed into the liquid reagent 122, is used for delivering the reagent. When pressurized inert gas 128 is delivered to the vessel 124 it pressurizes the head space 132 in the sealed vessel 124, thus pushing liquid out of the second tube (the delivery tube) 130.

As a method of controlling over-delivery of fluids which can occur with pneumatic delivery systems, the added features described below can be used to deliver small volumes of fluids without flooding. As shown in FIG. 27, an EWOD device is positioned (vertically) above the delivery tube 130 which is inserted into an EWOD loading position 60 on one end and which connects to the reagent vial at its other end. While the entire loading system 120 is shown in its preferential orientation, it is not necessary that it all be vertically disposed below the EWOD. To reach the EWOD device from the reagent vial, the fluid must travel at least some vertical distance upwards. The reason for such an arrangement is that the downward gravitational force on the liquid column directly below the EWOD inlet port provides a counteracting force that opposes the surface tension force that tends to flood the device. The Gas driving pressure is provided to the reagent vial 124 via a valve and a pressure regulator (not shown). Capacitive sensing 134 over the actuated EWOD electrodes is used to detect when the fluid has reached the device. An additional liquid sensor 136 can be provided to confirm the rise of the fluid meniscus 138. FIG. 27 shows the sensor 136 positioned a distance from the EWOD; it can be positioned closer to the EWOD or the delivery system can be operated without the sensor 136.

Another feature of the delivery systems is that instead of applying a steady pressure into the reagent vial 124, pulses of pressure are applied. The pulses of pressure can be applied either using one or more pneumatic control components such as pumps, valves, pressure regulators, flow controllers, or a combination thereof. When a sufficiently high pressure pulse is applied, the liquid in the tubing rises, with the higher pressure force counteracting the downward gravitational force to produce a net upward force. When the pressure is turned off (vented or reduced to a lower pressure), the gravitational force produces a net downward force, decelerating the meniscus 138 rise in the tubing and eventually causing it to fall. (It should be noted that while the capillary force would also figure in the force balance, it would remain constant during the meniscus 138 rise or fall in a uniform cross-section tubing and therefore simply be another offset of the gravitational force.) By oscillating the pressure, the meniscus 138 can be kept close to the chip, but with oscillating position so that the fluid momentum always remains low in either direction (toward or away from chip). This operation is illustrated in FIG. 28.

Another important feature of the technique is the sensing of the droplet at the EWOD device, prior to reaching the EWOD 98 or positioned on the heater 100. Several mechanisms could be used for the sensing, e.g. electrical, chemical, electrochemical, thermal, optical etc. or a combination thereof. As soon as a sufficient amount of liquid is sensed to be positioned on the EWOD device, the pressure is dropped, allowing gravity to pull the liquid back. Since the momentum of the rising liquid was not allowed to build up beyond one pulse width, the overshoot in volume, if any, is limited and flooding is avoided. EWOD actuation can be turned on over some or all the wetted region on the device in order to hold some of the reagent fluid on the EWOD device, while the rest of the fluid is pulled back. In order to improve the accuracy of droplet volume dispensed, a secondary on-chip droplet dispenser can be used to create droplets from the loaded volume.

There is inherent robustness in this approach, which is tolerant of variations of the pneumatic control, as well as the properties, such as wetting properties, of the liquid being delivered and surface characteristics of the materials used in fabrication of the EWOD. Firstly, a system relying purely on pneumatic control has limited precision over the volume of liquid dispensed. Due to the compressibility of the inert gas 128 in the system, there can be a significant lag between the time the pressure control valve is actuated and the time the pressure actually changes at the surface of the fluid. The momentum built up during the fluid movement prior to pneumatic valve closure (when attempting to "stop" the flow) can lead to "overshoot" during this lag time. While this effect can be avoided by the use of a slow flow rate to nudge the fluid flow slowly forward, this is often not practical in terms of factors such as time required and precision of pressure regulation, as well as phenomena like contact angle hysteresis and contact line pinning at the leading edge. Additionally, the possibility of uncontrolled fluid flow is further amplified for non-aqueous solutions often required in chemical synthesis, because these materials can be more wetting of the EWOD device than water. Following introduction of the droplet into the EWOD device, as the droplet volume increases, a wetting droplet experiences a greater surface tension force (proportional to the interfacial length) which results in the liquid being pulled into the chip, thus providing a positive feedback that could lead to a runaway volume delivered to the chip (a process referred to as flooding). As a result, many previously available microfluidic systems employ on-chip or off-chip liquid valves to achieve greater precision over start and stop of liquid flow. However, on-chip valves are not available in EWOD systems, and off-chip liquid valves are expensive as well as not disposable, and would require cleaning after each use.

It is therefore desirable to automate the delivery of reagents to the EWOD chip to increase ease of use and to protect the operator from exposure to radiation. Many methods exist for pumping liquid from a reagent reservoir to the chip. The challenge is determine when the initial gas has been removed from the delivery system and when the liquid arrives at the desired location. While accurate metering pumps and knowledge of the system geometry can be beneficial in improving delivery control, the use of volatile solvents also introduces uncertainty into the exact position of the liquid meniscus and the droplet size that reaches the heater position. Evaporation occurs from the end of the needle/tubing/etc. into the open space of the EWOD chip; a significant fraction of a unit-droplet-volume can evaporate within minutes. Thus, real-time sensing of liquids is desirable.

It has been suggested by others that liquid sensing can be accomplished in EWOD chips by measuring capacitance, but these techniques also require optical observation using a high resolution CCD camera or expensive capacitance meters. Disclosed herein is a capacitive sensing technique that uses greatly simplified hardware and software. This real-time liquid sensing system is designed to sense, quantify and identify liquids on the EWOD chip without requiring additional hardware, other than a single resistor, to be added to the EWOD chip or control system that is already used. The measurement is performed using AC signals and a phase-locked loop technique to extract the measured signal with high signal-to-noise ratio and a volume accuracy as small as picoliters.

Figure 32:
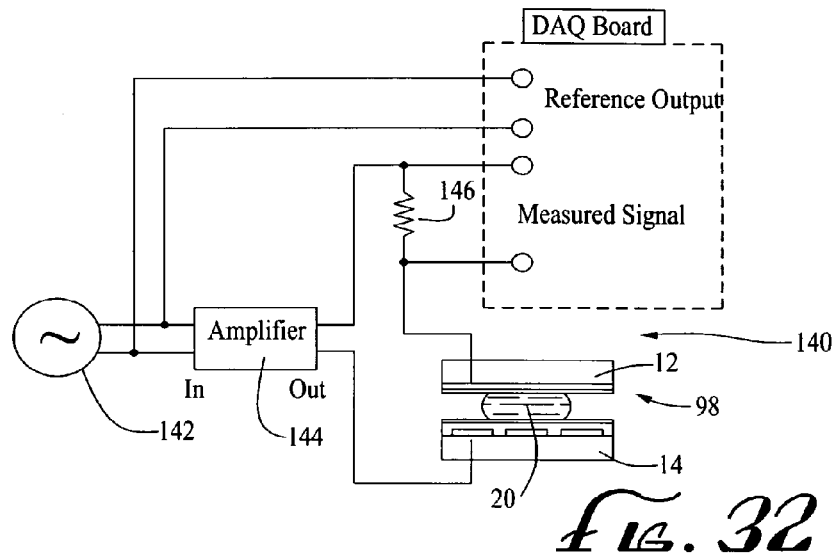
FIG. 32 is a schematic diagram of an EWOD control system for sensing droplet volume.
Figure 33:
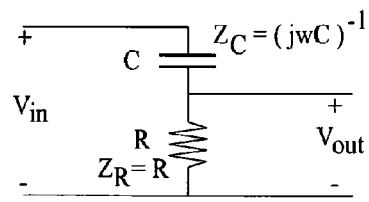
FIG. 33 is a schematic diagram of a circuit used for theoretical prediction of the relationship between voltage and capacitance (impedance).

In the EWOD control system 140, such as shown in FIGS. 32 and 33, a signal generator 142 and amplifier 144 generates a high voltage (100-200V) signal (1-20 kHz). Individually addressable relays apply this voltage selectively to the desired electrodes to move the fluid. To perform sensing in the feedback system, one small resistor 146 (approximately 1 kΩ) is added at the ground line in controlling circuit and the voltage is measured across the resistor instead of directly measuring the capacitance (FIG. 32). This resistor does not appreciably change the voltage across the liquid. To perform a capacitance measurement, the EWOD electrode is activated (with AC signal) at the site where measurement is desired. The out of phase voltage signal across the external resistor is measured via an analog-to-digital converter to determine the volume of liquid at the site of the active EWOD electrode. A phase locked loop (using unamplified sinusoidal signal as a reference) extracts the desired signal. Approximating the system as a parallel plate capacitor (see FIG. 33), it can be shown that the signal is a constant plus a term that is linearly proportional to the fraction of the electrode area covered with liquid, from which volume can be determined as it is linearly proportional to the dielectric constant minus one (which depends on the liquid), when the electrode size and gap spacing are known. Data collected for droplets of water and DMSO of different volumes (measured via CCD imaging), confirm the linear relationship. Once the electrode is completely covered with liquid, the signal saturates and a further increase in droplet volume cannot be detected.

If it is desired to measure capacitance at more than one site simultaneously, instead of inserting a single resistance on the ground line, one can instead insert resistors on the desired individual high-voltage electrode lines.

In summary, advantages of this approach for monitoring reagent loading to an EWOD chip, include, but are not limited to:

Minimal hardware addition to the EWOD system (A single precision resistor)

The measurement of voltage is performed at one point in the circuit tor all electrodes, while liquid sensing selectivity spatial precision is provided by EWOD's normal operating condition of activating a single electrode at a time The system requires no additional signal generation for measurement, as the frequency specific measurement is provided by the applied AC potential used for normal EWOD operation The measurement is based on the lock-in amplification technique, which essentially filters out all noise outside a narrow frequency band of interest. As such the system is immune to major contributing noise factors such as drifts, 60 Hz noise and ground loops The low noise design allows accurate measurement of liquid volumes onto the EWOD chip as small as a pico-liter using readily available 16 bit digitizers and without incorporating low noise amplification The systems responsiveness (as fast as 1 ms for 10 nl accuracy) and accuracy (down to 1 pico-liter for 100 ms response time) can easily be adjusted using software The software can very quickly indicate the presence of liquid, which has many practical applications for chemical reactions performed on EWOD, and then refine its accuracy of volume measurement and liquid identification as needed and depending on time available.

Described above are methods for synthesis of [$^{18}$F]FNB and [$^{18}$F]FDG. In both cases, there are several steps where droplets are completely dried, i.e., solvent evaporated, before proceeding with the next step. However, if all the liquid is allowed to evaporate, the heat conduction path from the bottom of the chip assembly, where heater is located, to the top of the chip assembly (i.e., the cover plate 58) is broken. As a result the top is substantially cooler than the controlled temperature. Any solid or liquid residue on the top portion will thus experience a different temperature profile than that on the bottom. This can lead to some unreliability of processes such as [$^{18}$F]fluoride drying.

To ensure a more uniform and controllable temperature, the synthesis process was modified so that complete evaporation never occurs. For example, during the process of drying the [$^{18}$F]fluoride, new droplets of MeCN were continually added (which were then transported to the heater site) to replenish what was evaporating. In one example, fresh droplets were loaded every 10-20 seconds for 5 min. Radiosynthesis of [$^{18}$F]FDG and [$^{18}$F]FTAG was successfully performed with yields comparable to conventional synthesis approaches, suggesting that this modified drying process was successful at removing traces of water and ensuring a reactive [$^{18}$F]fluoride complex.

EXAMPLE 3

Materials and Characterization

Figure 26:
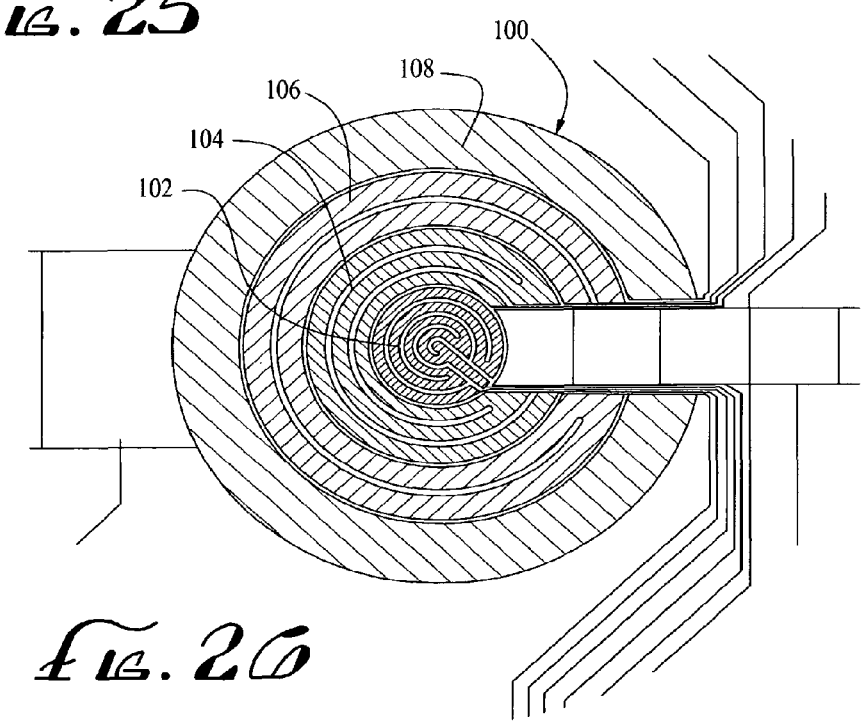
FIG. 26 is an enlarged diagram of the concentric heater of FIG. 25.

Anhydrous acetonitrile (MeCN, 99.8%), anhydrous dimethyl sulfoxide (DMSO, 99.9%), potassium carbonate (99%), mannose triflate for PET imaging and 4,7,13,16,21,24,-hexaoxa-1,10, diazobicyclo(8.8.8) hexacosane 98% (K 2.2.2) were obtained from Sigma-Aldrich and used as received without further purification. 1 N HCl (certified, Fisher Chemicals) were purchased from Fisher Scientific and used as received. Synthesis was performed with EWOD chip 98 having 4 concentric circular heater electrodes 102, 104, 106, 108 (FIGS. 25, 26).

Synthesis:

No-carrier-added [$^{18}$F]fluoride ion was generated by irradiation of 97% $^{18}$O-enriched water with an 11 MeV proton beam using an RDS-112 cyclotron (Siemens). 50 μL (20 mCi) of the aqueous [$^{18}$F]fluoride ion was added to a 40 μL mixture of K 2.2.2 (26 mM) and $K_2CO_3$ (7 mM) in MeCN:$H_2O$ (98:2 v/v). Mannose triflate (5 mg; 0.01 mmoles) was dissolved in anhydrous DMSO (100 μL) to obtain a concentration of 104 mM. The [$^{18}$F]fluoride mixture (2 μL) was pipetted onto the EWOD chip 98 through a dedicated loading position 60 at the edge of the cover plate 58 and transported to the heater 100 via electrowetting forces. This loading process was repeated 3 additional times. The 8 μL [$^{18}$F]fluoride mixture was gradually evaporated on the dedicated EWOD heater 100 at 105° C. and then heated for an additional 3 minutes. Additional 8 μL of the [$^{18}$F]fluoride mixture was loaded and evaporated in the same manner as previously described. The [$^{18}$F]fluoride mixture were dried via azeotropic distillation by transporting five MeCN droplets (3 μL) through a first loading position 60 into the heater 100 site and heated at 105° C. for 3 minutes. This drying step was repeated 2 additional times. Two droplets of mannose triflate in DMSO (2 μL; 104 mM) were pipetted onto the EWOD chip 98 through a second loading position 60 to avoid cross-contamination. Six MeCN droplets (3 μL) were then loaded and transported to the heater 100 to initiate the fluorination reaction. The reaction droplet was gradually heated from room temperature to 120° C. over a period of 15 minutes. Four droplets of HCl (2.5 μL; 1 N) were added to the crude [$^{18}$F]FTAG droplet and the combination was transported to the heater 100 region to perform the hydrolysis reaction. The reaction droplet was heated at 90° C. for 10 mins. After the synthesis, the cover plate 58 was removed and the crude [$^{18}$F]FDG product was extracted using 30 μL of $H_2O$ for radio-TLC analysis and cartridge purification. The crude [$^{18}$F]FDG was spotted onto a TLC silica plate and was developed in 95:5 MeCN/$H_2O$ solvent mixture. The percent composition of [$^{18}$F]FDG and the unreacted [$^{18}$F]fluoride were analyzed using a radio-TLC (MiniGITA star, Raytest). The conversion efficiency of the radiolabeling was analyzed to be 46% and the hydrolysis efficiency was 100%.

Figure 29:
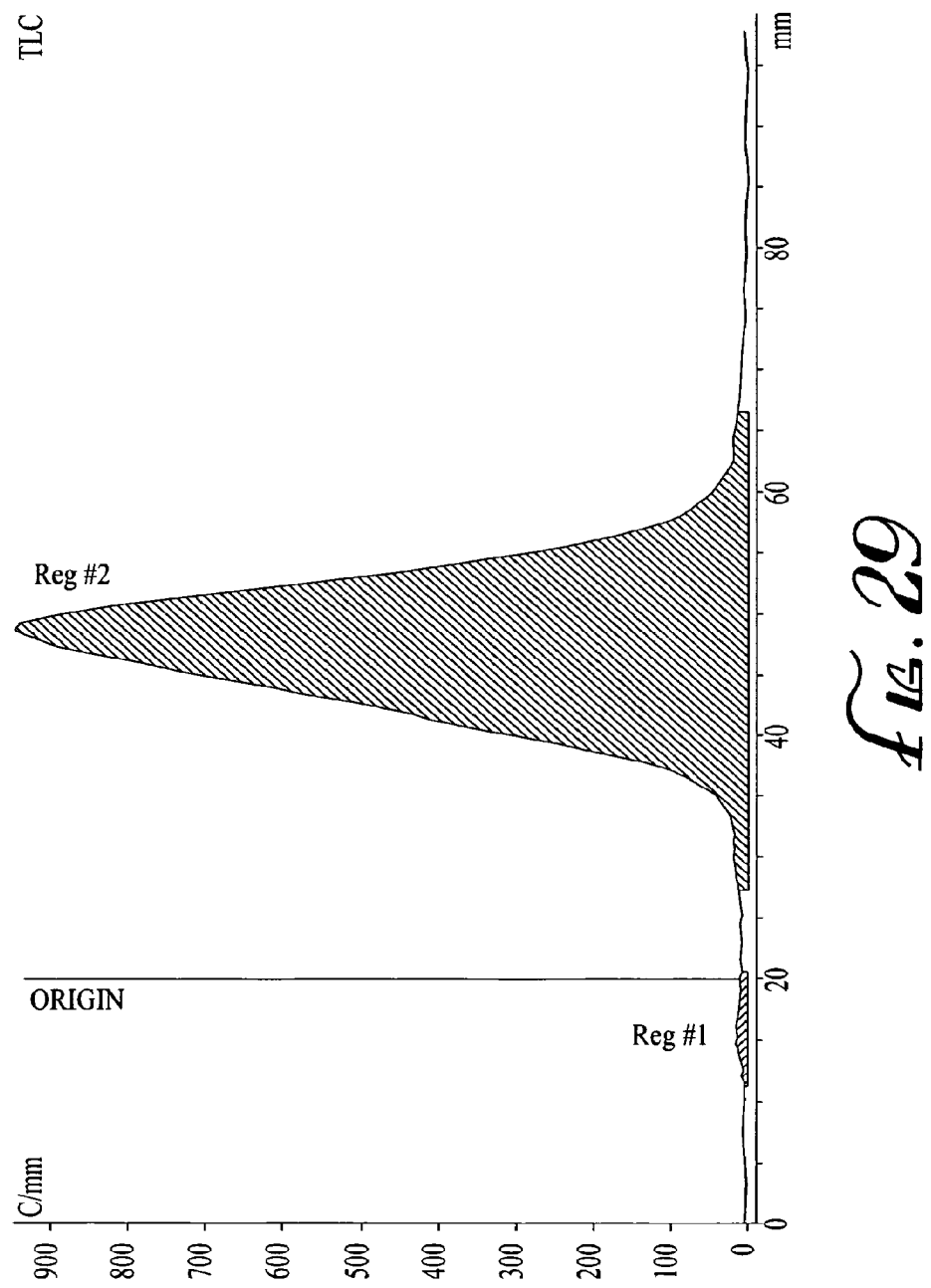
FIG. 29 is a TLC graph showing the results of the production of a preclinical dose of [$^{18}$F]FDC purified using a mini-cartridge.

Cartridge Purification:

The crude [$^{18}$F]FDG microdroplet 20 synthesized on the EWOD microfluidic chip 98 was purified using a purification cartridge modified to avoid dilution of the final end product used in micro-PET imaging. Commercially available purification cartridges consist of 280 mg to several grams of resin suited for macroscale synthesis with several milliliters of sample volumes and therefore are not designed for the microvolumes generated in the above procedure. Single dosage PET probes synthesized on the EWOD chip consisted of several microliters of crude sample, which would be lost within the large amount of resin in a standard cartridge. Therefore, custom-made purification cartridges were prepared by packing AG-50W-X4 (4 mg) and AG11 A8 (4 mg) resins with 50-100 mesh size (BioRad Laboratories) and neutral alumina (10 mg) with particle size 50-300 μm (Waters) within a 3.175 mm ID polyurethane tubing. The resins were sandwiched between 2 polyethylene frits (20 pun pore size) that were fitted with barb-to-luer adapters. The cartridge was first conditioned with water (1 mL; 18 MΩ) by gravity drip. The 30 μL crude product in water was pipetted and passed through the cartridge by applying pressure using a 1 mL syringe. 30 μL of water was then used to flush the cartridge. The sample eluent that was collected after the first cartridge purification was spotted on a TLC plate and the radiochemical purity was found to be 85% by radio-TLC. The [$^{18}$F]FDG mixture was therefore passed through a second miniaturized cartridge packed with only neutral alumina (50 g) in the similar manner as previously described. The chemical purity after the second cartridge purification was analyzed using the radio-TLC and found to be 99% (FIG. 29).

The purified product was then injected into mice for micro-PET imaging with resulting images matching images taken from mice injected with [$^{18}$F]FDG produced by conventional means.

EXAMPLE 4

DMSO is not commonly used in the macroscale radiosynthesis of [$^{18}$F]FDG due to the low vapor pressure of DMSO and the difficulty of removal. High-temperatures (which can damage the tracer) and long times (which results in substantial radioactive decay) are needed when using evaporative removal. A cartridge can also be used, but results in substantial increase in final volume which can be a problem especially for preclinical imaging. On the other hand DMSO provides high solubility of a wide range of organic compounds, high polarizability and the ability to perform chemical reactions at higher temperature (due to its high boiling point). Using an EWOD chip 98 incorporating features of the invention set forth herein, reliable radiofluorination of mannose triflate with no-carrier-added [$^{18}$F]fluoride in DMSO followed by acid hydrolysis, has been successfully demonstrated for the production of [$^{18}$F]FDG. In micro-droplet radiosynthesis, in which 2-15)μL of DMSO is used during a typical radiofluorination reaction, the majority of the DMSO is evaporated at 120° C. after 10 minutes of the reaction. Subsequently, acid was added to the crude intermediate to perform the hydrolysis reaction to yield [$^{18}$F]FDG with quantitative hydrolysis efficiencies. This result showed that the residual DMSO in the reaction droplet did not affect the hydrolysis reaction nor the micro-PET imaging of a mouse.

EXAMPLE 5

Figure 30:
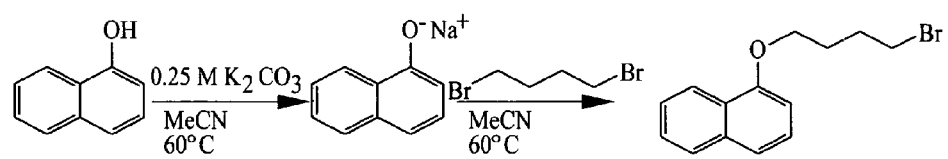
FIG. 30 shows the chemical reaction for the preparation of 1-(4-bromobutoxy) naphthalene.

To demonstrate the utility of the process and the EWOD chips 98 for chemical reactions other than radiochemistry, a simple chemical synthesis (not involving radioisotope) in a volatile organic solvent was performed using an EWOD chip. Due to the "open" structure of an EWOD chip, microliter droplets of organic solvents evaporate very rapidly, especially at elevated temperatures, before chemical reactions can occur. An approach utilized to allow the reactions to progress before the solvent is evaporated was to continually replenish the reaction site with new solvent droplets using the electrowetting mechanism to transport microliter volumes of solvent from a loading site 60 to the reaction site 100. A modified etherification reaction was performed between 1-napthol and dibromobutane in acetonitrile (MeCN; bp. 82° C.) to yield 1-(4-bromobutoxy) naphthalene. The reaction is shown schematically in FIG. 30. In this chemical synthesis, 1-napthol (74 mM; 2 μL) was first allowed to be reacted with $K_2CO_3$ (250 mM; 1 μL) in MeCN at 60° C. for 3 minutes. MeCN was continuously added to the reaction droplet to maintain a liquid phase reaction. Subsequently, dibromobutane solution in MeCN (3.7 M; 1 μL) was added to the reaction site and the substitution reaction was performed at 60° C. for 5 minutes.

Figure 31:
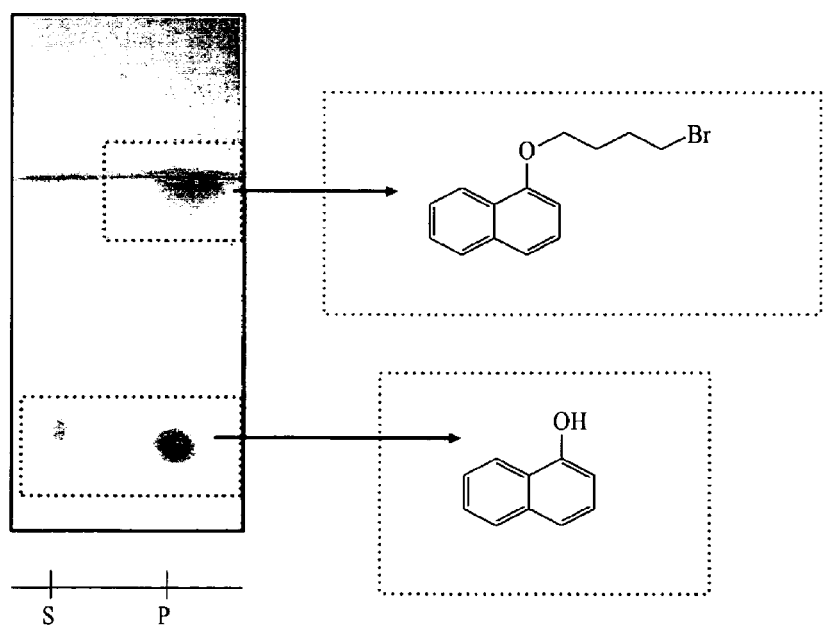
FIG. 31 illustrates the TLC separation of 1-(4-bromobutoxy)naphthalene.

After 5 minutes, the cover plate was removed, and the crude product was extracted using MeCN. The crude product, labeled as P, was spotted onto a TLC plate along with the starting material (labeled as S; 1-napthol) (FIG. 31). The TLC plate was developed in a solvent chamber containing dichloromethane/hexane (2:1 v/v) solvent mixture. The progress of the reaction was determined via tracking of the TLC stains using the UV light. Based on the TLC analysis, the substitution reaction on the EWOD chip yielded 1-(4-bromobutoxy) naphthalene, which appeared as a new spot with $R_f$ value of 0.9, while the unreacted 1-napthol had an $R_f$ value of 0.2.

We claim:

1. A method of performing radiosynthesis comprising:
   providing an electro-wetting-on-dielectric device (EWOD) comprising:
      a first substrate having one or more electrically defined fluid paths along a first surface thereof, each fluid path comprising discrete electrode pads, wherein adjacent electrode pads are separated from each other by non-conductive spaces, each of the electrode pads having electrically conductive lines attached thereto, each conductive line provided to deliver electrical signals to the conductive pad to which the line is attached to provide electrically directed movement of one or more fluid droplets along the fluid paths;
      one or more fluid delivery sites located on or adjacent to the one or more electrically defined fluid paths; and
      one or more process operation sites located along the electrically defined fluid paths on the first substrate;
   placing one or more fluid droplets comprising a radioisotope in a liquid carrier at one of the fluid delivery sites, the delivery site being spaced from the one or more operation sites,
   providing an electric field in a serial manner to the conductive pads adjacent to the fluid delivery sites to move the one or more fluid droplets comprising the radioisotope to one of the one or more process operation sites;
   placing one or more fluid droplets comprising at least one radiosynthesis reagent at one of the fluid delivery sites;
   providing an electric field in a serial manner to the conductive pads adjacent to the fluid delivery sites to move the one or more fluid droplets comprising the radiosynthesis reagent to one of the one or more process operation sites;
   reacting at least one of the radiosynthesis reagents with the radioisotope at one or more process operation sites;
   recovering the reaction product from the EWOD device.

2. The method of claim 1, wherein the reacting process comprises mixing of the one or more fluid droplets comprising the radioisotope with one or more fluid droplets comprising the at least one radiosynthesis reagent.

3. The method of claim 1, wherein the reacting process comprises heating of the one or more fluid droplets comprising the radioisotope with one or more fluid droplets comprising the at least one radiosynthesis reagent.

4. The method of claim 1, wherein the one or more fluid droplets comprising the radioisotope are evaporated prior to reacting with the at least one radiosynthesis reagent.

5. The method of claim 1, wherein the at least one radiosynthesis reagent comprises a precursor.

6. The method of claim 1, wherein the one or more fluid droplets comprising the radioisotope and the one or more fluid droplets comprising the at least one radiosynthesis reagent comprise volumes within of less than 1 mL.

7. The method of claim 1, wherein the process operation site comprises a heater.

8. The method of claim 1, wherein the reaction product comprises a Fluorine-18 containing molecule.

9. A method of performing Fluorine-18 radiosynthesis comprising:
   providing an electro-wetting-on-dielectric device (EWOD) comprising:
      a first substrate having one or more electrically defined fluid paths along a first surface thereof, each fluid path comprising discrete electrode pads, wherein adjacent electrode pads are separated from each other by non-conductive spaces, each of the electrode pads having electrically conductive lines attached thereto, each conductive line provided to deliver electrical signals to the conductive pad to which the line is attached to provide electrically directed movement of one or more fluid droplets along the fluid paths;
      one or more fluid delivery sites located on or adjacent the one or more electrically defined fluid paths; and
      one or more heater sites located along the electrically defined fluid paths on the first substrate;
   placing one or more fluid droplets comprising [$^{18}$F]fluoride in a liquid carrier at one of the fluid delivery sites, the delivery site being spaced from the one or more heater sites,
   providing an electric field in a serial manner to the conductive pads adjacent to the fluid delivery sites to move the one or more fluid droplets comprising [$^{18}$F]fluoride to one of the one or more heater sites;
   evaporating the one or more fluid droplets comprising [$^{18}$F]fluoride at the one or more heater sites;
   placing one or more fluid droplets comprising a precursor containing in an organic liquid carrier at one of the fluid delivery sites;
   providing an electric field in a serial manner to the conductive pads adjacent to the fluid delivery sites to move the one or more fluid droplets comprising the precursor to the heater sites containing the evaporated [$^{18}$F]fluoride;
   heating the heater sites containing the evaporated [$^{18}$F]fluoride and the precursor to generate a reaction product; and
   recovering the reaction product from the EWOD device.

10. The method of claim 9, wherein evaporating the one or more fluid droplets comprising [$^{18}$F]fluoride at the one or more heater sites comprises adding a plurality of droplets of an anhydrous organic solvent while the one or more heater sites are actively heating the one or more fluid droplets comprising [$^{18}$F]fluoride.

11. The method of claim 10, wherein the anhydrous organic solvent comprises anhydrous acetonitrile.

12. The method of claim 9, further comprising:
   placing one or more fluid droplets comprising a hydrolysis agent at one of the fluid delivery sites;
   providing an electric field in a serial manner to the conductive pads adjacent to the fluid delivery sites to move the one or more fluid droplets comprising the hydrolysis agent to the heater sites containing the reaction product.

13. The method of claim 9, wherein the precursor comprises mannose triflate.

* * * * *